US008975383B2

(12) United States Patent
Yumioka et al.

(10) Patent No.: US 8,975,383 B2
(45) Date of Patent: Mar. 10, 2015

(54) PROTEIN REFOLDING METHOD

(75) Inventors: Ryosuke Yumioka, Kawasaki (JP); Daisuke Ejima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1158 days.

(21) Appl. No.: 12/941,272

(22) Filed: Nov. 8, 2010

(65) Prior Publication Data

US 2011/0077384 A1    Mar. 31, 2011

Related U.S. Application Data

(63) Continuation-in-part of application No. PCT/JP2009/058304, filed on Apr. 27, 2009.

(30) Foreign Application Priority Data

May 8, 2008 (JP) ................................ 2008-122536

(51) Int. Cl.
| C07K 1/113 | (2006.01) |
| C07K 1/14 | (2006.01) |
| C07K 14/54 | (2006.01) |
| C07K 14/475 | (2006.01) |
| C12N 9/10 | (2006.01) |
| C07K 16/18 | (2006.01) |
| C07K 16/44 | (2006.01) |

(52) U.S. Cl.
CPC ........... *C07K 14/5412* (2013.01); *C07K 1/1136* (2013.01); *C07K 1/145* (2013.01); *C07K 14/475* (2013.01); *C12N 9/104* (2013.01); *C07K 16/18* (2013.01); *C07K 16/44* (2013.01); *C07K 2317/569* (2013.01); *C07K 2317/64* (2013.01); *C12N 9/1044* (2013.01)
USPC .......................................... 530/412; 435/69.1

(58) Field of Classification Search
None
See application file for complete search history.

(56) References Cited

U.S. PATENT DOCUMENTS

| 6,034,224 | A | 3/2000 | Storrs et al. |
| 6,410,694 | B1 | 6/2002 | Storrs et al. |
| 6,756,482 | B1 | 6/2004 | Ono et al. |
| 7,501,495 | B2 | 3/2009 | Ejima et al. |
| 2002/0058792 | A1 | 5/2002 | Storrs et al. |
| 2002/0090675 | A1 | 7/2002 | Yokoyama et al. |
| 2005/0176109 | A1 | 8/2005 | Yumioka et al. |
| 2008/0318300 | A1 | 12/2008 | Koyama et al. |

FOREIGN PATENT DOCUMENTS

| CN | 1786017 | 6/2006 |
| CN | 101113174 | 1/2008 |
| EP | 0263902 | 4/1988 |
| WO | WO87/00204 | 1/1987 |
| WO | WO98/29433 | 7/1998 |
| WO | WO99/61474 | 12/1999 |
| WO | WO00/40706 | 7/2000 |

OTHER PUBLICATIONS

Fan et al, Journal of Colloid and Interface Science, 2008, vol. 321, pp. 227-234.*
Karabormi et al, Science, 1994, vol. 266, pp. 254-256.*
Kudou, M., et al., "A novel protein refolding system using lauroyl-L-glutamate as a solubilizing detergent and arginine as a folding assisting agent," Protein Expression and Purification 75 (2011) pp. 46-54.
Kane, J. F., et al., "Formation of recombinant protein inclusion bodies in *Escherichia coli*," Trends Biotechnol. 6, 95-101 (1988).
Mitraki, A., et al., "Protein folding intermediates and inclusion body formation," Bio/Technology 7, 690-697 (1989).
Schein, C.H., "Production of soluble recombinant proteins in bacteria," Bio/Technology 7, 1141-1149 (1989).
Burgess, R.R. "Refolding solubilized inclusion body proteins," Methods Enzymol. 463, 259-282 (2009).
Tsumoto, K., et al., "Practical considerations in refolding proteins from inclusion bodies," Protein Exp. Purif. 28, 1-8. (2003).
Singh, S.M., et al., "Solubilization and refolding of bacterial inclusion body proteins," J. Biosci. Bioeng. 99, 303-310 (2005).
Middelberg, A.P.J. "Preparative protein refolding," Trends in Biotechnol. 20, 437-443 (2002).
Cabrita, L.D., et al., "Protein expression and refolding—A practical guide to getting the most out of inclusion bodies," Biotechnol. Annu. Rev. 10. 31-50 (2004).
Cleland, J.L., et al.,"Polyethylene glycol enhanced protein refolding," Bio/Technology 10, 1013-1019 (1992).
Defelippis, M.R., et al., "Evidence for a self-associating equilibrium intermediate during folding of human growth hormone," Biochemistry 32, 1555-1562 (1993).
Buchner, J., et al., "Renaturation, purification and characterization of recombinant Fab-fragments produced in *Escherichia coli*," Bio/Technology 9, 157-162. (1991).
Tsumoto, K., et al., "Highly efficient recovery of functional single-chain Fv fragments from inclusion bodies overexpressed in *Escherichia coli* by controlled introduction of oxidizing reagent— application to a human single-chain Fv fragment," J Immunol Methods. 219, 119-129 (1998).
Zardeneta, G., et al., "Detergent, liposome, and micelle-assisted protein refolding,". Anal. Biochem. 223, 1-6 (1994).
Patra, A.K., et al., "Optimization of inclusion body solubilization and renaturation of recombinant human growth hormone from *Escherichia coli*," Protein Exp. Purif. 18, 182-192 (2000).

(Continued)

*Primary Examiner* — Karen Canella
(74) *Attorney, Agent, or Firm* — Shelly Guest Cermak; Cermak Nakajima & McGowan LLP

(57) ABSTRACT

The present invention provides a method for producing a protein which has a restored native higher-order structure by bringing a protein which has lost its native higher-order structure into contact at pH 6.5 to 9.0 with a 1 to 3% aqueous solution of a specific surfactant, such as lauroylglutamic acid to obtain a solubilized solution of the protein; and then adding the solubilized solution to a buffer with pH 6.5 to 9.0 containing arginine or an arginine derivative at a concentration of 0.1 to 1.2 M to lower the concentration of the specific surfactant, such as lauroylglutamic acid, in the obtained mixture solution down to 0.02 to 0.275%. According to the present invention, it is possible to easily restore the native higher-order structure of a protein while smoothly removing the surfactant from the protein.

2 Claims, 14 Drawing Sheets

(56) References Cited

OTHER PUBLICATIONS

Burgess, R.R. "Purification of overproduced *Escherichia coli* RNA polymerase σ factors by solubilizing inclusion bodies and refolding from Sarkosyl," Methods Enzymol. 273, 145-149 (1996).
Wetlaufer, D.B., et al., "Control of aggregation in protein refolding: a variety of surfactants promote renaturation of carbonic anhydrase II," Protein Sci. 4, 1535-1543 (1995).
Lu, D., et al., "Molecular dynamics for surfactant-assisted protein refolding," J. Chem. Phys. 126, 0649061-13 (2007).
Lilie, H., et al., "Advances in refolding of proteins produced in *E. coli*," Curr. Opin Biotechnol. 9, 497-501 (1998).
Clark, E.D.B., et al., "Inhibition of aggregation side reactions during in vitro protein folding," Methods Enzymol. 309, 217-236 (1999).
Lange, C., et al., "Suppression of protein aggregation by L-arginine," Curr. Pharm. Biotechnol. 10, 408-414 (2009).
Tsumoto, K., et al., "Role of arginine in protein refolding, solubilization, and purification," Biotechnol. Prog. 20, 1301-1308. (2004).
Umetsu, M., et al., "How additives influence the refolding of immunoglobulin-folded proteins in a stepwise dialysis system. Spectroscopic evidence for highly efficient refolding of a single-chain Fv fragment," J. Biol. Chem. 278, 8979-8987 (2003).
Ejima, D., et al., "High yield refolding and purification process for recombinant human interleukin-6 expressed in *Escherichia coli*," Biotechnol. Bioeng. 62, 301-310 (1999).
Yokoyama, K., et al., "In vitro refolding process of urea-denatured microbial transglutaminase without pro-peptide sequence," Protein Exp. Purif. 26, 329-335 (2002).
Lili, W., et al., "Expression, renaturation and simultaneous purification of recombinant human stem cell factor in *Escherichia coli*," Biotechnol Lett. 28, 993-997 (2006).
Lenassi Zupan, A., et al., "High expression of green fluorescent protein in *Pichia pastoris* leads to formation of fluorescent particles," J. Biotechnol. 109, 115-122 (2004).
Tao, H., et al., "Purifying natively folded proteins from inclusion bodies using sarkosyl, Triton X-100, and CHAPS," BioTechniques, 48, 61-64 (2010).
Kurucz, I., et al., "Correct disulfide pairing and efficient refolding of detergent-solubilized single-chain Fv proteins from bacterial inclusion bodies," Mol. Immunol. 32, 1443-1452 (1995).
Jekabsons, M.B., et al., "Nucleotide binding to human uncoupling protein-2 refolded from bacterial inclusion bodies," Biochem J. 366, 565-571 (2002).
Takagi, T., et al., "Binding isotherms of sodium dodecyl sulfate to protein polypeptides with special reference to SDS-polyacylamide gel electrophoresis," J Biochem. 77, 939-947 (1975).
Reynolds, J.A., "The role of micelles in protein—detergent interactions," Methods Enzymol. 61, 58-62 (1979).
Puri, N.K., et al., "Solubilization of growth hormone and other recombinant proteins from *E. coli* inclusion bodies by using a cationic surfactant," Biochem. J., 285, 871-879 (1992).
Cardamone, M., et al., "A spectroscopic and equilibrium binding analysis of cationic detergent-protein interactions using soluble and insoluble recombinant porcine growth hormone," Biochim. Biophys. Acta 1206, 71-82 (1994).
Steele, J. C., et al., "Characterization of the apolipoprotein B polypeptide of human plasma low density lipoprotein in detergent and denaturation solutions," J. Biol. Chem. 254, 1633-1638 (1979).
Tandon, S., et al., "Detergent-assisted refolding of guanidinium chloride-denatured rhodanese. The effect of lauryl maltoside," J. Biol. Chem. 261, 15615-15618 (1986).
Machida, S., et al., "Cycloamylose as an efficient artificial chaperone for protein refolding," FEBS Lett. 486, 131-135 (2000).
Nomura, Y., et al., "Protein refolding assisted by self-assembled nanogels as novel artificial molecular chaperone," FEBS Lett. 553, 271-276. (2003).
Schneider, C. P., et al., "Investigation of cosolute-protein preferential interaction coefficients: new insight into the mechanism by which arginine inhibits aggregation," J. Phys. Chem. B 113, 2050-2058 (2009).
Arakawa, T., et al., "The effects of arginine on refolding of aggregated proteins: not facilitate refolding, but suppress aggregation,". Biochem. Biophys. Res. Commun 304,148-152 (2003).
Nakakido, M., et al., "To be excluded or to bind, that is the question: Arginine effects on proteins," Curr Pharm Biotechnol. 10, 415-420 (2009).
Arakawa, T., et al., "Suppression of protein interactions by arginine: a proposed mechanism of the arginine effects," Biophys Chem. 127, 1-8 (2007).
Fujii, T., et al., "Stable Supply of Large Amounts of Human Fab from the Inclusion Bodies in *E. coli*," J. Biochem. 2007;141:699-707.
Jungbauer, A., et al., "Folding and refolding of proteins in chromatographic beds," Curr. Op. Biotechnol. 15,487-494 (2004).
Matsubara, M., et al., "Achievement of renaturation of subtilisin BPN' by a novel procedure using organic salts and a digestible mutant of *Streptomyces subtilisin* inhibitor," FEBS Lett. 342,193-196(1994).
Singh, S., et al., "Solubilization and Refolding of Bacterial Inclusion Body Proteins," J. Biosci. Bioeng. 99, 303-310 (2005).
Rozema, D., et al., "Artificial Chaperone-assisted Refolding of Carbonic Anhydrase B" J. Biol. Chem. 271, 3478-3487 (1996).
Hagen, A.J., et al., "Protein Refolding in Reversed Micelles," Biotechnol. Bioeng. 35, 955-965 (1990).
Seefeldt, M.B., et al., "High-pressure studies of aggregation of recombinant human interleukin-1 receptor antagonist: Thermodynamics, kinetics, and application to accelerated formulation studies," Protein Science 14, 2258-2266 (2005).
Ramirez-Parra, E., et al., "Characterization of wheat DP, a heterodimerization partner of the plant E2F transcription factor which stimulates E2F-DNA binding," FEBS Lett. 486, 73-78 (2000).
Lanckriet, H., et al., "Operational Regimes for a Simplified One-Step Artifical Chaperone Refolding Method," Biotechnol. Prog. 20, 1861-1867 (2004).
De Bernardez Clark, E., "Refolding of recombinant proteins," Current Opinion in Biotechnology 1998;9(2):157-163.
Supplementary European Search Report for EP Patent App. No. 09742692.8 (Apr. 3, 2012).
Office Action from Chinese Patent App. No. 200980127827.6 (Nov. 28, 2012).

\* cited by examiner

REDOX SYSTEM GSH/GSSG (mM)
1: MOLECULAR-WEIGHT MARKERS(14, 20, 30, 43, 67, AND 94 kDa FROM BOTTOM)
2: SOLUBILIZED SOLUTION
3: BLANK
4: 5/1
5: 3/1
6: 2/1
7: 2/2
8: 1/1
9: 0.5/1
10: 1/2
11: 1/3

PROTEIN REFOLDING METHOD

The application is a continuation of, and claims priority under 35 U.S.C. §120 to, International Application No. PCT/JP2009/058304, filed Apr. 27, 2009 and claims priority therethrough under 35 U.S.C. §§119, 365 to Japanese Application No. 2008-122536, the entireties of which are hereby incorporated by reference herein.

BACKGROUND OF THE INVENTION

1. Field of the Invention

The present invention relates to a refolding method for restoring the native higher-order structure of a protein which has lost activity and/or stability as a result of becoming insoluble or losing its higher-order structure.

2. Brief Description of the Related Art

When preparing a recombinant protein using a production host, such as *E. coli*, the protein can become denatured and/or insoluble in water, also known as denatured. Often, the protein has also lost its activity and/or become destabilized. Therefore, the higher-ordered structure of its native state must be restored if the protein is to be used in a pharmaceutical preparation or the like. Protein refolding methods can be used in such cases.

However, reagents and methods used in refolding must be appropriately selected for each protein; therefore, such techniques can be difficult for a person with no experience in refolding. In addition, even for a person with sufficient experience, it still may be difficult to re-acquire the native state of a protein if the protein has a complicated higher-ordered structure and is likely to associate and/or aggregate during refolding.

In order to resolve these problems, several novel refolding methods have been proposed. For example, the following methods and combination methods or modified methods thereof have been reported: a column-refolding method in which the risk of association and/or aggregation is lowered by using a chromatography column (A. Jungbauer, W. Kaar, R. Schlegl: Current opinion in Biotechnology 15, 487-494 (2004)); an immobilized refolding method in which a target is bound to a carrier to prevent its association and/or aggregation (M Matsubara, et al.: FEBS LETT., 342, 193-196 (1994)); a pH extraction method in which a protein is solubilized in a partially-denatured state using an acidic or basic buffer instead of a denaturing agent (S. M. Singh and A. K. Panda: Journal of Bioscience and Bioengineering 99, 303-310 (2005)); a method in which a molecular chaperone is used in combination (D. Rozeman and S. H. Gellman: Journal of Biological Chemistry 271, 3478-3487 (1996)); a method in which an reversed micelle is used to exert a molecular chaperone-like function (A. J. Hagen, T. A. Hatton, and D. I. C. Wang: Biotechnol Bioeng. 35, 955-965 (1990)); a method in which a micelle of a surfactant is utilized (G. Zardeneta and P. H. Horowitz: Analytical Biochemistry 223, 1-6 (1994)); and a high-pressure refolding method in which extraction is carried out under an ultra-high pressure exceeding 3000 atmospheres without using any denaturing agent (M. B. Seefeldt, Y. S. Kim, J. Carpenter, T. W. Randolph: Protein Science 14, 2258-2266 (2005)).

The technique which has attracted the most attention among these is the "artificial chaperone system", which is a multi-stage refolding method. In this method, the objective protein is extracted with a denaturing agent and then diluted with a buffer containing a surfactant to recover a partial structure while preventing association and/or aggregation. In the next step, the surfactant is forcibly stripped from the protein with a surfactant binder, such as cyclodextrin, and the re-folded higher-order structure is formed. The advantage of this technique has been considered that it is possible to effectively prevent association and/or aggregation, which is the most serious problem, without carrying out trial-and-error experiments, simply by searching several conditions according to a predetermined method. A successful case in refolding by using this technique has been reported, and a modified method of this method has been continuously studied (S. Machida, S. Ogawa, S. Xiaohua, T. Takaha, K. Fujii, K. Hayashi: FEBS Lett. 486, 131-135 (2000)).

However, as the artificial chaperone system was increasingly used, the following facts and the like were revealed: the stripping of the added surfactant from the protein is not as easy as reported; and complicated experiments are still required in order to determine the appropriate re-folding conditions. In addition, the multi-stage operation complicates the process, and therefore limits the application to industrial-scale production (H. Lanckriet and A. P. J. Middelberg: Biotechnology Progress 20, 1861-1867 (2004)).

As described above, even the artificial chaperone system which has received the highest evaluation is not sufficient as a method which allows a person with no experience to easily and effectively carry out protein refolding.

Alternatively, a method has been reported for refolding a protein using acylated sarcosine. Acylated sarcosine cannot be stripped from a protein when simply diluted; therefore, the native higher-order structure of the protein cannot be restored unless the acylated sarcosine is removed by a special method (Richard Burgess: Methods in Enzymology. 273, 145-149 (1996), and EP 0263902 A). A method has also been reported of refolding in which insoluble bovine growth hormone is solubilized by a surfactant solution containing lauroyl-L-glutamic acid, and making the solution strongly alkaline, and then the concentration of the surfactant is lowered by ultrafiltration (U.S. Pat. No. 6,410,694). In this method, it is difficult to effectively restore the native state of any protein other than the growth hormone. In addition, when using a strong alkaline pH environment, the protein can be chemically changed, such as deamidation, which is irreversible.

SUMMARY OF THE INVENTION

Thus, it is an aspect of the present invention to provide a simple refolding method, which allows for the restoration of the protein's native higher-order structure while smoothly stripping away the surfactant from the protein.

A specific surfactant has been found to be easily stripped away from a denatured protein while the protein'native higher-order structure is restored. This can be done by solubilizing the denatured protein with an aqueous solution of the specific surfactant, and diluting this solubilized solution with a buffer containing arginine or an arginine derivative.

It is an aspect of the present invention to provide a method for producing a protein having a restored native higher-order structure the method comprising:

(1) bringing a protein which has become insoluble or lost its native higher-order structure into contact at pH 6.5 to 9.0 with a 1 to 3% aqueous solution of a surfactant selected from the group consisting of dicarboxylic acids having $C_8$ to $C_{16}$ acyl groups and salts thereof, decanoylsarcosine and salts thereof, decanoylalanine and salts thereof, decanoic acid and salts thereof, lauryltrimethylammonium chloride, and combinations thereof, to obtain a solubilized solution of the protein;

(2) adding the solubilized solution to a buffer with pH 6.5 to 9.0 comprising an additive selected from the group consisting of arginine, an arginine derivative, and combinations thereof, wherein said additive is at a concentration of 0.05 to 1.2 M, to lower the concentration of the surfactant to 0.02 to 0.5%, to obtain a mixture; and (3) recovering from the mixture the protein having a restored native higher-order structure.

It is a further aspect of the present invention to provide a method for restoring a native higher-order structure of a protein which has become insoluble or lost its native higher-order structure, the method comprising:

(1) bringing the protein which has become insoluble or lost its native higher-order structure into contact at pH 6.5 to 9.0 with a 1 to 3% aqueous solution of a surfactant selected from the group consisting of dicarboxylic acids having $C_8$ to $C_{16}$ acyl groups and salts thereof, decanoylsarcosine and salts thereof, decanoylalanine and salts thereof, decanoic acid and salts thereof, lauryltrimethylammonium chloride, and combinations thereof, to obtain a solubilized solution of the protein; and (2) adding the solubilized solution to a buffer with pH 6.5 to 9.0 comprising an additive selected from the group consisting of arginine, an arginine derivative, and combinations thereof, wherein said additive is at a concentration of 0.05 to 1.2 M, to lower the concentration of the surfactant to 0.02 to 0.5%, to obtain a mixture.

It is a further aspect of the present invention to provide a method for obtaining a protein having a restored native higher-order structure, the method comprising:

(1) bringing a protein which has become insoluble or lost its native higher-order structure into contact at pH 6.5 to 9.0 with a 1 to 3% aqueous solution of a surfactant selected from the group consisting of lauroylglutamic acid, lauroylaspartic acid, lauroyliminodiacetic acid, and combinations thereof, to obtain a solubilized solution of the protein; and (2) adding the solubilized solution to a buffer with pH 6.5 to 9.0 comprising an additive selected from the group consisting of arginine, an arginine derivative, and combinations thereof, wherein said additive is at a concentration of 0.1 to 1.2 M, to lower the concentration of the surfactant to 0.02 to 0.275%, to obtain a mixture.

It is a further aspect of the present invention to provide a method for restoring a native higher-order structure of a protein which has become insoluble or lost its native higher-order structure, the method comprising:

(1) bringing a protein which has become insoluble or lost its native higher-order structure into contact at pH 6.5 to 9.0 with a 1 to 3% aqueous solution of a surfactant selected from the group consisting of lauroylglutamic acid, lauroylaspartic acid, lauroyliminodiacetic acid, combinations thereof, to obtain a solubilized solution of the protein; and (2) adding the solubilized solution to a buffer with pH 6.5 to 9.0 comprising an additive selected from the group consisting of arginine, an arginine derivative, and combinations thereof, wherein said additive is at a concentration of 0.1 to 1.2 M, to lower the concentration of the surfactant to 0.02 to 0.275%, to obtain a mixture.

According to the present invention, it is possible to easily and effectively refold a protein without any experience in refolding methods or using any special device. According to the present invention, it is also possible to prevent association and/or aggregation of a protein which may occur during the refolding process.

Although not bound by any theory, it is considered as follows. A protein in general associates and/or aggregates as soon as a surfactant is stripped from the protein. In the meantime, according to the present invention, when a denatured protein is unfolded by using a specific surfactant and then diluted, and arginine or an arginine derivative is added to the thus obtained diluted solution, it is possible to prevent association and/or aggregation of the protein by the arginine or arginine derivative while allowing the specific surfactant to be detached from the protein.

DETAILED DESCRIPTION OF EXEMPLARY EMBODIMENTS

Protein

Figure 1:
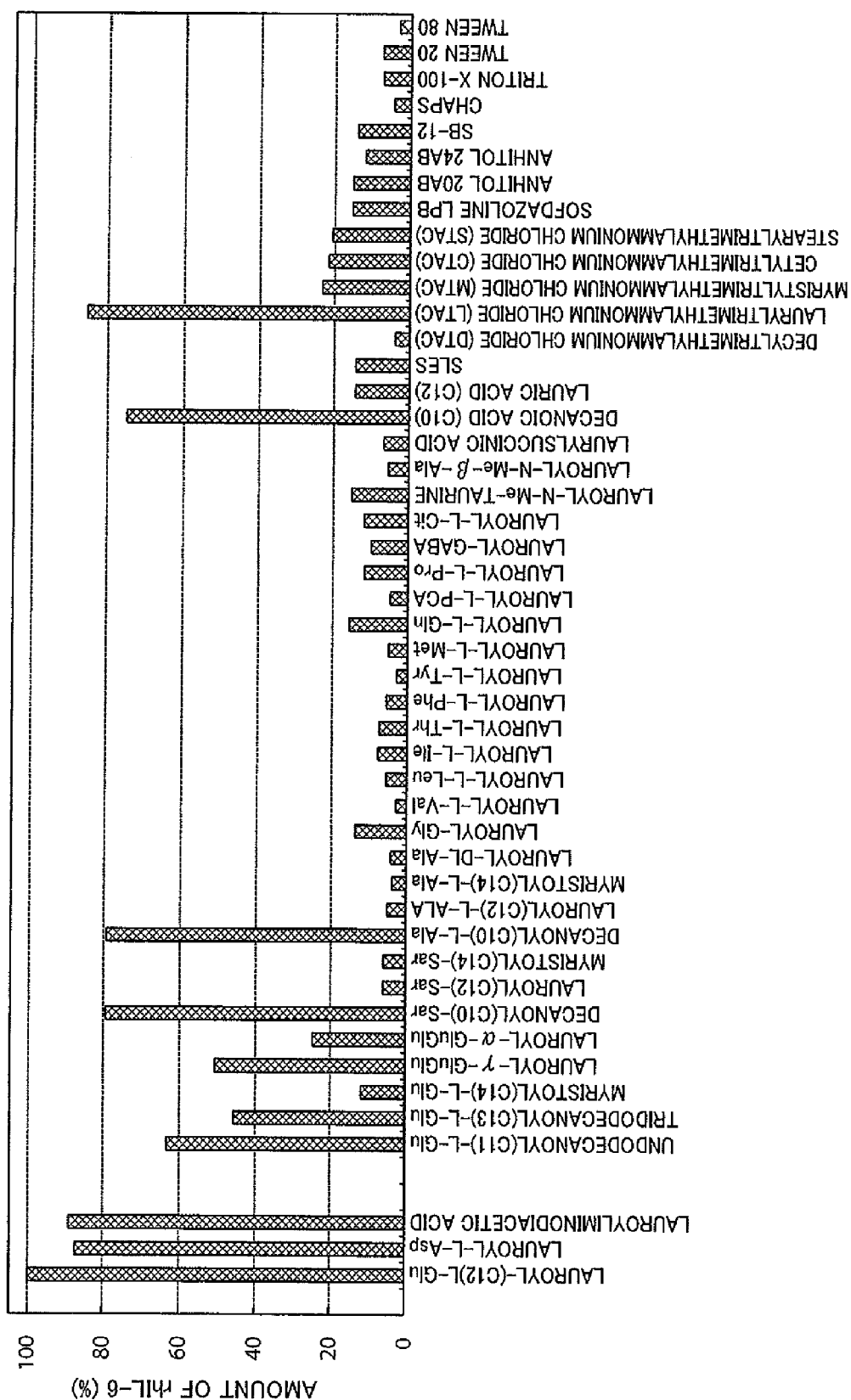
FIG. 1 shows the amounts of rhIL-6 solubilized by using various surfactants (Reference Example 1).

The protein which can be used in accordance with the presently disclosed subject matter can be a protein which has become insoluble or lost its higher-order structure. Proteins which have become insoluble and proteins which have lost their higher-order structure cannot be clearly distinguished from each other; therefore, a protein having a higher-order structure different from that of its native state can be used. Proteins can be used which have a secondary structure mainly composed of α-helixes (IL-6, for example), proteins which have a secondary structure mainly composed of β-sheets (scFv and Fab, for example), and proteins which have a secondary structure that includes both (transglutaminases, for example). Monomeric proteins (IL-6 and the like) and polymeric proteins (Fab and the like) can also be used. Proteins which have no intermolecular or intramolecular disulfide bonds (transglutaminases, for example) and proteins which have such bonds (IL-6, scFv, and Fab, for example) can also be used.

For example, an insoluble recombinant protein prepared in a microbial production host, such as *E. coli*, can be used, such as a protein having a solubility in 100 g of water of 0.001 g or below (at 25° C.), for example. A protein which had been soluble, but which has become insoluble due to some sort of stress, may also be used. The form of protein is not particularly limited, and may be granular, in powder form, or fibrous, for example. The characteristics of the primary structure and secondary structure of the protein do not impose any limitation. It does not matter whether a protein is monomeric or has an oligomer structure. A fragment of a protein can also be used. For example, a protein fragment having a weight-average molecular weight (measured by an ultracentrifugal method or a static light-scattering method, at room temperature) of 5000 daltons up to 150000 daltons can be used.

Specifically, examples include cytokines, such as human interleukin-6; ligand proteins, such as growth factors, various hormones, and differentiation inducers, which exert their functions once a specific higher-order structure has been acquired; enzymes, such as transglutaminases; enzyme inhibitor proteins; and antibody-related molecules having an immunoglobulin structure.

Examples of the antibody-related molecules include antibody fragments, such as fragments of variable region (Fv), single chain Fv (scFv), fragments of antigen binding (Fab), fragments of antigen binding (Fab'), and divalent fragments of antigen binding (F(ab')$_2$); artificial antibodies, such as bispecific single chain Fv and diabodies, and dimerized artificial minibodies obtained by fusion between a fragment of variable region and a part of a Fc domain; single-domain antibodies which are composed of a single domain derived from a light chain or a heavy chain of a domain constituting a fragment of antigen binding or a fragment of variable region; and Fc fusion proteins in which a protein or a peptide is fused to an antibody Fc domain.

More specifically, examples include the following in an insoluble form or in a form which has lost the higher-order structure, such as single chain Fv (scFv), such as HyHEL-10 scFv, which include Pexelizumab (scFv) for example; Abciximab (product name: ReoPro), ranibizumab (product name: LUCENTIS), and Certolizumab (product name: Cimzia) as fragments of antigen binding (Fab); Fc Fusion proteins, such as anti-Fluorescein scFv Fc fusion, which include romiplostim (product name: Nplate), rilonacept (product name: ARCALYST), abatacept (product name: ORENCIA), and alefacept (product name: AMEVIVE), for example; and the like. Particularly, antibody fragments can be used. The structures of these antibody-related molecules are described in detail in heretofore known articles, such as Holliger P. and Hudson P J. Nature Biotechnology 23 (9), 1126-1136 (2005).

Artificial affinity molecules created based on structures other than the immunoglobulin structure, such as ankyrin repeat, fibronectin type III domain, and lipocaline, as a scaffold structure may also be used.

The above-described protein which has either become insoluble or lost the higher-order structure can have an immunoglobulin structure in a domain thereof.

The above-described protein having an immunoglobulin structure in a domain thereof can be an antibody fragment having a part of an antibody domain, an artificial antibody, such as a diabody and a minibody, or a Fc fusion protein.

The above-described antibody fragment having a part of an antibody domain can be scFv, Fab, Fab', or (F(ab')$_2$).

The above-described Fc fusion protein can be obtained by fusion of a cytokine, a receptor extracellular domain, or a peptide to an antibody Fc domain.

Step (1): Solubilization of a Denatured Protein with a Surfactant

■ Type of Surfactant

Dicarboxylic acids having $C_8$ to $C_{16}$ acyl groups, decanoylsarcosine (lauroylsarcosine, lauroyl-Sar), decanoylalanine (lauroylalanine, lauroyl-Ala), decanoic acid, and salts thereof (sodium salts and potassium salts, for example), lauryltrimethylammonium chloride (LTAC), and mixtures thereof can function as a surfactant (solubilizing agent) which is capable of unfolding in water a protein into a non-native form after becoming insoluble or losing its higher-order structure.

The surfactant can be a dicarboxylic acid having $C_8$ to $C_{16}$ acyl groups, decanoylsarcosine, decanoylalanine, or a salt thereof. The surfactant can be exemplified by a dicarboxylic acid having $C_8$ to $C_{16}$ acyl groups or a salt thereof. Further examples of the dicarboxylic acid having $C_8$ to $C_{16}$ acyl groups can be lauroylglutamic acid (lauroyl-Glu), lauroylaspartic acid (lauroyl-Asp), or lauroyliminodiacetic acid.

Lauroyl-Glu, lauroyl-Asp, lauroyl-Sar, and lauroyl-Ala can have any one of a D form, an L form, and a DL form. When the protein which has either become insoluble or lost its higher-order structure is a cytokine, such as IL-6, or an enzyme, such as transglutaminase, lauroyl-Glu, lauroyl-Asp, lauroyliminodiacetic acid, a salt thereof, or a mixture thereof can be used. As the surfactant, lauroyl-L-Glu is a particular example, since it is superior in its ability to solubilize all kinds of insoluble proteins, and can be easily removed without continuing to adsorb to the protein when diluted, as well as being available in highly-pure reagent form at a moderate price.

■ Concentration of Surfactant

Lauroyl-Glu, lauroyl-Asp, lauroyliminodiacetic acid, lauroyl-Sar, lauroyl-Ala, decanoic acid, or LTAC can be used in the form of a 1 to 3% aqueous solution thereof, a 1.5% to 2.8% aqueous solution thereof, or a 1.75 to 2.5% aqueous solution thereof, for example. Within these concentration ranges, it is possible to sufficiently increase the efficiency of protein solubilization while keeping the dilution rate in the next step at an appropriate level.

■ pH

The pH of the aqueous solution at 25° C. can be selected to be a moderate condition of pH 6.5 to 9.0, or pH 7.0 to 8.5, in accordance with properties of the denatured protein. Incidentally, pH can be measured by a pH meter equipped with a pH electrode. The pH can be adjusted using alkali, such as sodium hydroxide. A buffer can be used as the aqueous solution.

■ Temperature and Time Period of Contact

A thus prepared aqueous solution of a surfactant and a denatured protein are brought into contact with each other to obtain a solubilized protein solution. The denatured protein can be added to the aqueous solution of the surfactant, or the aqueous solution of the surfactant can be added to the denatured protein. The contact can be carried out allowing the thus obtained mixture to stand at 5 to 40° C., or at 15 to 40° C. These ranges can be chosen because cleavage due to a chemical reaction and modifications such as oxidation can be kept to a minimum. The mixture can be left to stand for a period of time of normally 0.1 to 3.0 hours, or 0.5 to 1.0 hour(s). These ranges can be chosen because cleavage due to a chemical reaction and modifications such as oxidation can be kept to a minimum. The thus obtained mixture may be stirred while standing.

The amount of the denatured protein or the solubilized aqueous solution can be adjusted to achieve a concentration of the solubilized protein of 1 to 20 mg/ml, since in this way the concentration of the protein is not drastically lowered in the following dilution step.

It can be confirmed whether the protein is solubilized or not by visual examination of turbidity or an UV absorption spectrum method at 280 nm, for example.

Step (2): Dilution with Additive Solution

■ Dilution Rate

Subsequently, the solubilized solution is diluted with a buffer containing an additive of arginine or an arginine derivative at a dilution rate of 10 to several tens, and maintained in situ until the protein's native higher-order structure. The solubilized solution is diluted to achieve a concentration of the surfactant after the dilution of 0.02 to 0.5%, 0.04 to 0.35%, or 0.05 to 0.30%. The surfactant is immediately stripped from the protein by this dilution, and therefore the protein forms a higher-order structure. The dilution may be carried out in an appropriately-selected form of single stage, multi stage (step gradient), or linear gradient.

When the protein is a cytokine, such as IL-6, or an enzyme, such as transglutaminase, the dilution can be carried out to achieve a concentration of the surfactant after the dilution of 0.02 to 0.275%, 0.04 to 0.125%, or 0.05 to 0.10%.

When the protein is an antibody fragment, especially in the case of scFv, the dilution rate can be smaller than that for above-described cytokines and enzymes. Specifically, the dilution can be carried out to achieve the concentration of the surfactant after the dilution of 0.02 to 0.5%, 0.05 to 0.4%, or 0.1 to 0.3%. However, even if the concentration of the surfactant falls below these levels, the protein's native higher-order structure can be restored as long as the concentration is within the ranges specified.

In the cases of Fab, Fab', and F(ab')2 among the above-described antibody fragments, the dilution may be carried out in a single stage, or in multiple stages of at least two stages. Multi-stage dilution can be used because the percentage of refolding can be further improved. In the case of single-stage dilution, the dilution can be carried out to achieve a concentration of the surfactant after the dilution of 0.02 to 0.08%, 0.03 to 0.07%, or 0.04 to 0.06%. In the case of multi-stage dilution, dilution in the first stage may be carried out at a dilution rate in the same range as that for the above-described scFv. The dilution in the last stage can be carried out to achieve the concentration of the surfactant after the dilution of 0.02 to 0.08%, 0.03 to 0.07%, or 0.04 to 0.06%. The dilution can be carried out gradationally. In that case, the dilution can be carried out to achieve the final concentration after the dilution of 0.02 to 0.08%, 0.03 to 0.07%, 0.04 to 0.06%.

The dilution can be carried out within these ranges because restoration of the protein's native higher-order structure can be facilitated and stability of the protein can be achieved. It can be confirmed whether the protein's native higher-order structure has been restored, by a spectrometry, such as a CD spectrometry and a fluorescence spectrometry, a method, such as HPLC, in which physicochemical properties of a protein are observed, or using indicators of higher-order structure, such as enzymatic activity.

■ Type of Additives

Additives such as arginine can have either an L form or a D form, and can form a salt with an inorganic acid, such as a hydrochloride salt, or a salt with an organic acid, such as an acetate salt. Examples of the arginine derivative include arginines with an acyl group having 1 to 6 carbon atoms, such as acetylarginine and N-butyroylarginine; agmatine obtained by removing the carboxyl group; and arginine acid obtained by introducing a hydroxyl group in the place of the $\alpha$-amino group. For the arginine derivative, acylated arginine can be used, and N-butyroylarginine is a particular example. An arginine hydrochloride is a particular example of the additive.

■ pH

As a buffer, sodium phosphate, sodium citrate, tris (tris-hydroxymethylaminomethane) hydrochloride, or the like can be used. The pH should be suitable for the properties of the objective protein, and is generally a neutral pH within pH 6.5 to 9.0. Accordingly, the pH in Step (2) should be within this range, and therefore can be different from the pH in Step (1). The pH can be adjusted by using hydrochloric acid, sodium hydroxide, and/or the like.

■ Concentration of Additive

The concentration of the additive can be selected in accordance with the properties of the objective individual protein, and can be 0.05 to 1.2 M, 0.06 to 1.0 M, or 0.08 to 0.8 M. These ranges can be used because the protein's native higher-order structure can be restored and the following purification step is not disturbed.

In the case where the protein is a cytokine, such as IL-6, or an enzyme, such as transglutaminase, the concentration of the additive can be 0.1 to 1.2 M, 0.2 to 1.0 M, or 0.4 to 0.8 M. In the case where the protein is an antibody fragment, particularly scFv, the concentration of the additive can be 0.2 to 1.0 M, or 0.4 to 0.8 M.

In the cases of Fab, Fab', and F(ab')2 among the above-described antibody fragments, the concentration of the additive can be 0.05 to 0.3 M, or 0.08 to 0.12 M. When the dilution is carried out in at least two stages, dilution in the first stage can be carried out at a dilution rate which is in the same range as that for the above-described scFv. Dilution can be carried out in the last stage to achieve a concentration of the additive after the dilution of 0.05 to 0.3 M, 0.06 to 0.2 M, or 0.08 to 0.12 M. The dilution can be carried out in an appropriately-selected form of single stage, multi stage (step gradient), or linear gradient.

■ Dilution Temperature and Incubation Time

The dilution may be carried out at room temperature, or at 5 to 10° C. if the objective protein is not heat stable in its native state. For example, in the case of human interleukin (rhIL-6), it should be diluted with a solution of an additive, and then incubated at room temperature for approximately 1 minute. In the case of transglutaminase, it should be incubated at room temperature for 2 hours or more. When incubating at 5 to 10° C., it is necessary to carry out the incubation for a longer time.

In general, the time required for the incubation at a higher temperature is shorter. When the objective protein is an antibody-related molecule, it is better to incubate at a lower temperature for a longer time as compared to the incubations times and temperatures for IL-6 and cytokines, such as IL-6 and transglutaminase. In this way, the percentage of refolding can be further improved. Incubation at 5 to 48° C. for 1 hour to 5 days is an example.

In particular, when the antibody-related molecule is an antibody fragment, especially in the case of sdFv, incubation can be carried out at 5° C. to 15° C., 7° C. to 13° C., or 8° C. to 12° C., for 10 hours to 24 hours, 12 hours to 20 hours, or 15 to 18 hours. Association and aggregation of antibody-related molecules are inhibited during the incubation.

Thereafter, the diluted solution may be heated and incubated for another several hours to several days. The incubation can be carried out at 15° C. to 48° C., 20° C. to 46° C., or 23° C. to 45° C., for 1 hour to 5 days, 1.5 hours to 3 days, or 2 hours to 24 hours.

When the antibody fragment is Fab, Fab', or F(ab')2, the incubation can be carried out at 5 to 15° C. for 10 to 72 hours for a single-stage dilution. In another example, the incubation can be carried out at 7 to 13° C. for 12 to 20 hours. For a multi-stage dilution, the dilution in the first stage can be carried out at 5° C. to 15° C., 7° C. to 13° C., or 8° C. to 12° C., for 10 hours to 24 hours, 12 hours to 20 hours, or 15 hours to 18 hours. Association and aggregation of the antibody-related molecules are inhibited during the incubation.

Thereafter, the diluted solution may be heated and incubated for another several hours to several days, at 15° C. to 48° C., 20° C. to 46° C., or 23° C. to 45° C., for 1 hour to 5 days, 1.5 hours to 3 days, or 2 hours to 24 hours. The temperature can be adjusted in an appropriately-selected form of single stage, multi stage (step gradient), or linear gradient.

The dilution may be conducted gradually, over 10 to 72 hours at 5 to 15° C.

When the dilution is carried out in several stages, the concentration of the protein after dilution in the last stage can be maintained at 0.05 to 1.0 mg/ml, 0.1 to 0.5 mg/ml, or 0.15 to 0.3 mg/ml, by concentrating using an ultrafiltration membrane, for example, after the dilution in the last stage in order to cancel out the dilution rate, thereby facilitating formation of disulfide bonds among heavy chains and light chains of Fab.

Incidentally, in previously reported refolding of antibody-related molecules, the percentage of refolding is low because of the different rates of refolding among the different domains of the molecules, which results in a greater probability of association and/or aggregation during the refolding. In order to solve this problem, Tsumoto et al. proposed a refolding method in a stepwise dialysis system (The Journal of Biological Chemistry 278 (11), 8979-8987 (2003)). This method has been excellent due to the ability of the method to prevent the loss of protein due to association and/or aggregation that frequently occurs in a simple dilution method or the like. In this method, a highly-concentrated protein denaturing agent (guanidine chloride) is slowly removed from the solution of the denatured protein (single-chain antibody variable fragment, scFv) gradually in a six-stage dialysis operation. However, with six stages of dialysis, this method requires a long time for refolding; therefore, there are concerns that the protein may be chemically modified during the refolding, or an intermediate structure may be formed which is highly likely to aggregate. Ueda et al. has made possible refolding of a fragment of antigen binding (Fab) by modifying a part of the method by Tsumoto et al. (The Journal of Biochemistry 141 (5), 699-707 (2007)). In this method, an extended period of time as long as 130 hours is required for carrying out a four-stage dialysis, and the highest percentage of refolding is 24%; therefore, the method has not been considered to be an efficient refolding method.

However, as described above, the time period required for refolding an antibody-related molecule can be appropriately determined for each antibody-related molecule by gel filtration, HPLC, electrophoresis, or activity measurement of the antibody-related molecule. In many cases, the required time period is approximately 40 hours, and has been greatly shortened as compared to previously reported refolding methods of antibody-related molecules, which are represented by the stepwise dialysis system.

[Optional Step (A): Dilution Before Dilution with Additive Solution]

Prior to the dilution within the above-described ranges, some proteins may be diluted in advance by adding a phosphate buffer or the like. Specifically, between Step (1) and Step (2) described above, dilution can be carried out to achieve the concentration of a surfactant of 0.8% to 1.5%, or for example, 1%. The percentage of restoration of the native higher-order structure of an objective protein can be further increased by incubating the resulting solution after the dilution at 5 to 40° C., or 5 to 30° C., at room temperature, for example, for 0.5 hours or longer. Incubation for a time period in the same range as the time required for the solubilization or longer should be sufficient. In one example, the dilution can be carried out to achieve a concentration of the surfactant of 0.8 to 1%, and to incubate the diluted solution at 5 to 40° C. for 30 minutes or longer.

In particular, when a target protein is an antibody-related molecule and the antibody-related molecule is an antibody fragment, particularly the case of sdFv, the incubation can be carried out at 5° C. to 15° C., 7° C. to 13° C., or 8° C. to 12° C., for 10 hours to 24 hours, 12 hours to 20 hours, or 15 hours to 18 hours. During the incubation, the antibody-related molecule becomes closer to the native state without a progression of association and/or aggregation.

When the antibody fragment is Fab, Fab', or F(ab')2, dilution can be carried out with a buffer containing arginine or an arginine derivative as an additive to adjust the concentration of lauroyl-Glu to be 0.05 to 0.5%, 0.08 to 0.4%, or 0.1 to 0.3%, and the concentration of arginine to be 0.6 to 1.2 M, 0.7 to 1.1 M, or 0.8 to 1.0 M.

The pH of the thus obtained diluted solution at 25° C. should be in a range from pH 6.5 to 9.0, and therefore may be different from that in Step (1). The pH can be adjusted using hydrochloric acid, sodium hydroxide, and/or the like.

The concentration of the protein which has a restored higher-order structure in the dilution can be as high as 0.02 to 1 mg/ml depending on the amount and properties of the protein used in the dilution and the dilution rate.

[Optional Step (B): Formation of Disulfide Bond]

In some proteins, there may a disulfide bond within a single molecule, or, in the case of oligomeric proteins, there may an intermolecular disulfide bond. Formation of these disulfide bonds can be facilitated by a redox reaction of the proteins, which can improve the percentage of refolding.

The redox reaction may be carried out by adding a redox reagent which facilitates a thiol-disulfide exchange reaction, and thereby allows formation of an intramolecular or intermolecular disulfide bond (for example, a mixture of oxidized glutathione (GSSG) and reduced glutathione (GSH), a mixture of cystine and cysteine, a mixture of cystamine and cysteamine, a mixture of oxidized glutathione or cystine and mercaptoethanol, or the like), or copper ion which facilitates air oxidation, or may be carried out by changing the redox potential of the protein. Use of a redox reagent is one example.

The redox reaction may be carried out any time after Step (1) above, and may be carried out by adding a redox reagent together with an additive to the solubilized solution in Step (2) above, or may be carried out after a diluted solution is obtained in Step (2) above by adding a redox reagent to the diluted solution.

The concentration of a redox reagent or copper ion is adjusted to an appropriate level for each protein to be restored to the native state.

The pH at 25° C. at this stage should be in a range from pH 6.5 to 9.0. The pH can be adjusted using hydrochloric acid, sodium hydroxide, and/or the like, for example.

The temperature of the solution can be in the same range as the temperature of the solubilized solution obtained in Step (1), or be in the same range as the temperature of the solubilized solution obtained in Step (2). A temperature of 5 to 48° C. is one example for facilitating the redox reaction.

After the redox reaction, the solution may be incubated at 5 to 48° C. for approximately 1 hour to 5 days (120 hours).

The percentage of refolding achieved by the described method can be at least 30%, and can be as high as 70% in many cases.

[Optional Step (C): Purification]

The protein with restored higher-order structure can be purified by a standard method, such as ultrafiltration, dialysis, ion-exchange chromatography, gel-filtration chromatography, hydrophobic interaction chromatography, reverse-phase chromatography, and affinity chromatography.

Hereinafter, the present invention will be specifically described by using Examples. However, the present invention is not limited to these Examples.

EXAMPLES

Reference Example 1

As a protein, human interleukin-6 (rhIL-6: Japanese Patent No. 3200850) prepared from a recombinant *E. coli* strain was used. The rhIL-6 is insoluble in water (solubility to 100 g of water at 25° C.: 0.001 g or less), and is in a granular form. Aliquots of the insoluble granules containing 4 mg of rhIL-6 were each put into an Eppendorf tube (made of polypropylene: available from Eppendorf Co., Ltd.). The amount of rhIL-6 in the insoluble granules was quantified in advance by the reverse-phase HPLC method described in a published report (Japanese Patent No. 3200850).

To each of these, a surfactant prepared in advance to be 5% in pure water (Milli Q water) were appropriately added to achieve a final concentration of lauroyl-L-Glu, lauroyl-L-Asp, lauroyliminodiacetic acid, decanoylSar, decanoyl-L-Ala, decanoic acid, or lauryltrimethylammonium chloride of 2% and the rhIL-6 extraction concentration of 4 mg/ml, and the final volume of 1 ml was adjusted to 1 ml. The mixture was incubated at room temperature for 2 hours, thereby extracting rhIL-6 from the insoluble granules and solubilizing rhIL-6.

For comparison, the same operation was carried out using the surfactants listed below. When using an anionic surfactant, the concentration of the solution was adjusted to pH 7.0 (at 25° C.) using NaOH.

The surfactants used for comparisons: undecanoyl L-Glu, tridecanoyl L-Glu, myristoyl L-Glu, lauroyl-DL-Glu, lauroyl-γ-Glu-Glu, lauroyl-α-Glu-Glu, decanoyl-L-Asp, decanoyl-DL-Asp, myristoyl Sar, lauroyl-L-Ala, myristoyl-L-Ala, lauroyl-DL-Ala, lauroyl-Gly, lauroyl-L-Val, lauroyl-L-Leu, lauroyl-L-Ile, lauroyl-L-The, lauroyl-L-Phe, lauroyl-L-Tyr, lauroyl-L-Met, lauroyl-L-Gln, lauroyl-L-PCA, lauroyl-L-Pro, lauroyl-L-GABA, lauroyl-L-Cit, and lauryl-succinic acid (all of above were prepared at AJINOMOTO CO., INC.); lauroyl-Sar (available from Nacalai Tesque, Inc.); POE(20) sorbitan monooleate (Tween-80: available from Nacalai Tesque, Inc.); POE(9,10) p-t-octylphenyl ether (Triton X-100: available from Nacalai Tesque, Inc.); POE(20) sorbitan monopalmitate (Tween-20: available from Bio-Rad Laboratories, Inc.); lauroyl-N-Me-taurine (Nikkol LMT: available from Nikko Chemicals Co., Ltd.); lauroyl N-Me-β-Ala (available from Kawaken Fine Chemicals Co., Ltd.); amidopropylhydroxy sulfobetaine laurate (Sofdazoline LPB: available from Kawaken Fine Chemicals Co., Ltd.); decyltrimethylammonium chloride, myristyltrimethylammonium chloride, stearyltrimethylammonium chloride, and lauric acid (all of above were available from Tokyo Chemical Industry Co., Ltd.); cetyltrimethylammonium chloride (available from Wako Pure Chemical Industries, Ltd.); SLES (Sodium lauryl ether sulfate, Emal 270 D/B: available from Kao Corporation); laurylaminobetaine (Amphitol 20AB: available from Kao Corporation); myristylaminobetaine (Amphitol 24 AB: available from Kao Corporation); laurylsulfobetaine (SB-12: available from Sigma-Argininedrich Co.); and 3-[(3-cholamidopropyl)dimethylammonio]-1-propanesulfonate (CHAPS: available from Dojindo Laboratories).

To each extract, reduced glutathione and oxidized glutathione were added to achieve final concentrations of 10 μM and 2 μM, respectively. The mixture was incubated at room temperature overnight to form an intramolecular disulfide bond. The formation of the disulfide bond was confirmed with an indicator, which is a change in peak retention time in a reverse-phase HPLC method (column: Vydac 214-TP5410 (Separations Group); eluent: A/0.1% TFA, B/0.1% TFA+80% acetonitrile; flow rate: 1 ml/min; elution condition: linear gradient from 30% B to 50% B at 1.0%/min.). An aliquot of 50 μl of the obtained solution was diluted 20 times with 950 μl of a solution of 10 mM sodium phosphate (pH 7.0 at 25° C.) (the final volume of 1 mL; the final concentration of the surfactant of 0.1%).

Since it is known that a peak with the same retention time as that of a rhIL-6 preparation (Japanese Patent No. 3200850) in ion-exchange chromatography is derived from rhIL-6 with a native higher-order structure (Biotechnology and Bioengineering 62, 301-310 (1999)), the amount of rhIL-6 having a native higher-order structure contained in a solution obtained after the dilution described above was measured using ion-exchange HPLC (column: SP-NPR (available from Tosoh Corporation); eluent: A/0.01 M sodium acetate, pH 5.0, B/0.5 M sodium acetate, pH 5.5; flow rate: 1 ml/min; elution condition: linear gradient from 20% B to 70% B at 10%/min.).

The relative amounts of rhIL-6 solubilized using lauroyl-L-Asp and lauroyliminodiacetic acid, respectively, to the amount of rhIL-6 solubilized using lauroyl-L-Glu as a surfactant, which is set to 100%, are shown (FIG. 1). The relative amounts of rhIL-6 solubilized with the surfactants for comparison are shown as well (FIG. 1).

As clearly shown in FIG. 1, the amounts of rhIL-6 which were solubilized using lauroyl-Asp or lauroyliminodiacetic acid and then restored to a native higher-order structure were equivalent to the amount of rhIL-6 which was solubilized using lauroyl-Glu and then restored the native higher-order structure. The amounts of rhIL-6, which were restored to the native higher-order structure obtained when using these three surfactants, were higher than when using the other comparative surfactants.

The amounts of rhIL-6 restored to its native higher-order structure obtained when using lauroyl-Sar and cetyltrimethylammonium chloride (CTAC), which were frequently used in protein refolding in the past, were low at 5% and 21%, respectively. The amounts of rhIL-6 restored to is native higher-order structure obtained when using anionic surfactants and ampholytic surfactants, such as lauryl ether sulfate Na (SLES) and lauric acid, which were expected to be capable of extracting rhIL-6 from the insoluble granules containing rhIL-6, were low at below 20%. Nonionic surfactants, such as Tween 20, Tween 80, and Triton X-100, which are often used in refolding due to their inability to denature proteins, were largely unable to extract rhIL-6 from the granules, and were hardly capable of dissolving the insoluble granules; therefore, the amounts of rhIL-6 restored to the native higher-order structure were low at 3 to 5%.

Reference Example 2

It was investigated whether lauroyl-L-Glu, lauroyl-L-Asp, and lauroyliminodiacetic acid were effective in restoration of the native higher-order structure of the insoluble rhIL-6, even if the concentration of rhIL-6 to be subjected to extraction from the insoluble granules and solubilization thereafter was increased. For comparison, the following surfactants were used: lauryltrimethylammonium chloride, which resulted in an amount of rhIL-6 of 80% or more as compared to that of lauroyl-L-Glu in Reference Example 1; lauroyl-Sar, which has the same lauroyl group; undecanoyl-L-Glu, tridecanoyl-L-Glu, and myristoyl-L-Glu, which were used for confirmation of the effect of the length of the acyl chain in lauroyl-L-Glu; and decanoic acid, which was used for confirmation of the effect of the acyl chain.

Aliquots of 13 mg of the same insoluble granules of rhIL-6 as used in Reference Example 1 were each put into an Eppendorf tube. The surfactants were added to the respective Eppendorf tubes to achieve a final concentration of 2%, thereby obtaining 1 ml of 10 mM sodium phosphate solution, pH 7.0 (at 25° C.). The solution was incubated at room temperature for 2 hours at pH 7.0, thereby extracting rhIL-6 from the insoluble granules and solubilizing rhIL-6. The concentration of the extraction was adjusted to 13 mg/ml as a result. Similarly to Reference Example 1, reduced glutathione and oxidized glutathione were added to achieve final concentrations of 10 µM and 2 µM, respectively, and the resulting mixture was incubated at room temperature overnight to form an intramolecular disulfide bond.

An aliquot of 25 µl of the obtained solution was diluted 40 times with 975 µl of 10 mM sodium phosphate aqueous solution (pH 7.0 at 25° C.) (the final volume of 1 ml; the final concentration of the surfactant of 0.05%). In the same manner as that described in Reference Example 1, the amount of rhIL-6 which was forming a higher-order structure was measured using ion-exchange HPLC. The result is shown in FIG. 2.

Figure 2:
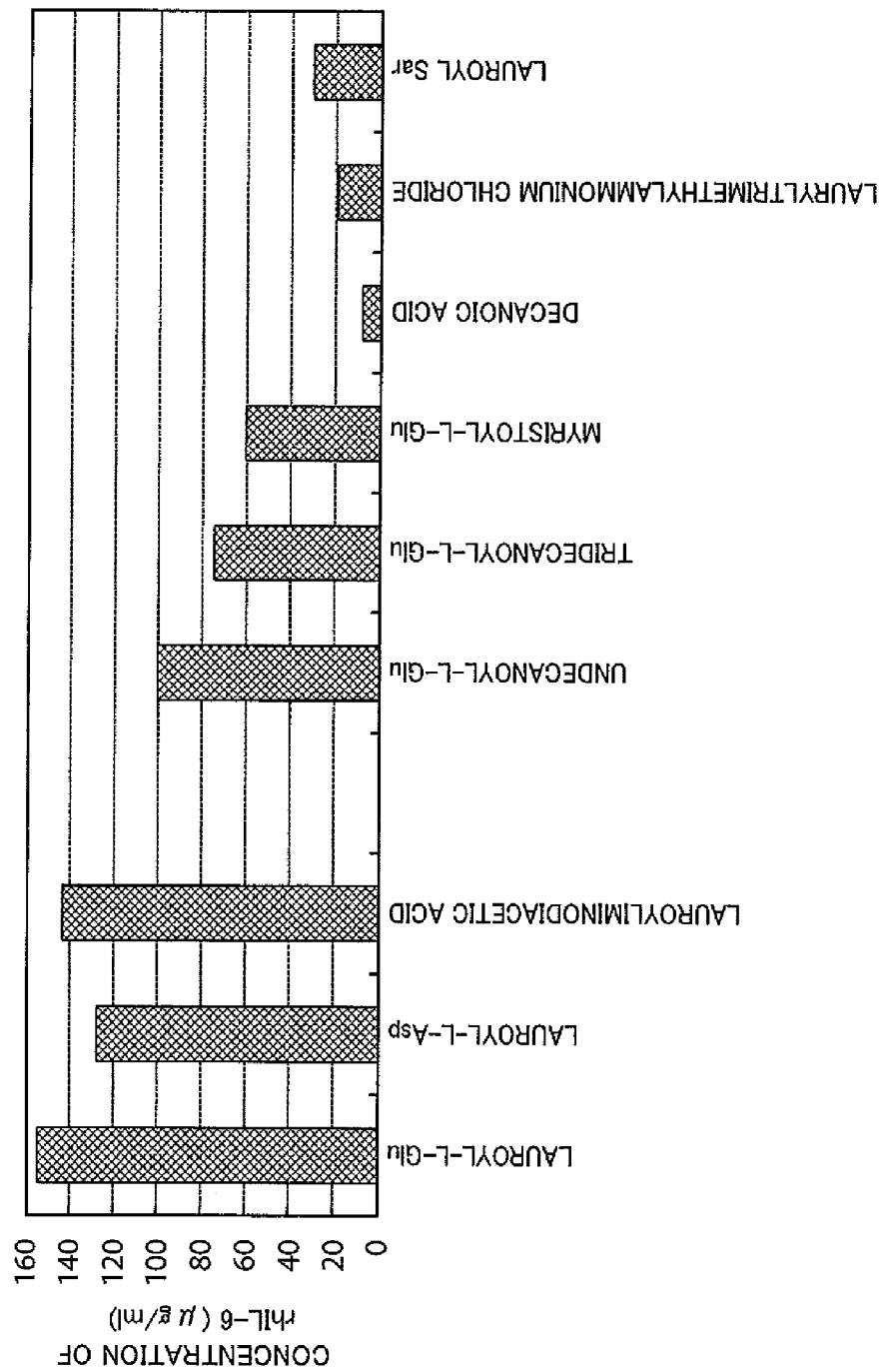
FIG. 2 shows the amounts of rhIL-6 solubilized by using various surfactants (Reference Example 2).

As clearly shown in FIG. 2, the concentration of rhIL-6 which restored the higher-order structure of the native state was highest when lauroyl-L-Glu was used, and a high concentration of rhIL-6 was also observed when single-chain surfactants having two hydrophilic portions, such as lauroyl-L-Asp and lauroyliminodiacetic acid, which have an intramolecular amido bond. When the length of the acyl chain of lauroyl-L-Glu was shorter down to C11 (undecanoyl) or longer up to C13 (tridecanoyl) or C14 (myristoyl), the concentration of rhIL-6 was lower as compared to when using lauroyl-L-Glu. Accordingly, it was found that C12 (lauroyl) is the most suitable length of the acyl chain. Only a small amount of rhIL-6 was recovered when decanoic acid having only an acyl chain was used. Lauroyl-Sar which had been found to be effective in refolding of G-CSF (Granulocyte colony-stimulating factor; U.S. Pat. No. 5,849,883) and growth hormone (EP0263902 A) was clearly inferior to lauroyl-L-Glu.

Reference Example 3

The concentration of surfactant for extracting rhIL-6 from the insoluble granules for solubilization was investigated.

Aliquots of 12.6 mg of the same water-insoluble granules of rhIL-6 as used in reference Example 1 were each put into an Eppendorf tube. A solution of lauroyl-L-Glu was added to the Eppendorf tubes to respectively achieve final concentrations of Lauroyl-L-Glu of 1.5%, 1.75%, 2.00%, 2.25%, and 3.00%, and thereby 3 ml of each solution of 10 mM sodium phosphate, pH 7.0 (25° C.) were added. The solutions were incubated at room temperature for 2 hours, thereby extracting rhIL-6 from the insoluble granules and solubilizing rhIL-6. If rhIL-6 was completely extracted, the concentration of the extraction of rhIL-6 would be adjusted to 4.3 mg/ml as a result.

After the extraction, 10 mM dithiothreitol (DTT) was added to a supernatant, and the supernatant containing DTT was adjusted to pH 8 and then heated at 37° C. for 30 minutes to reduce the disulfide bond. The supernatant was then subjected to reverse-phase HPLC (column: Vydac 214-TP5410 (Separations Group); eluent: A/0.1% TFA, B/0.1% TFA+ 80% acetonitrile; flow rate: 1 ml/min.; elution condition: linear gradient of 30% B to 50% B at 1.0%/min.), thereby measuring the amount of solubilized rhIL-6 from the insoluble granules (Biotechnology and Bioengineering 62, 301-310 (1999)). The amounts of rhIL-6 at the respective concentrations relative to the amount of rhIL-6 when the final concentration of lauroyl-L-Glu was 3.00% are shown in FIG. 3.

Figure 3:
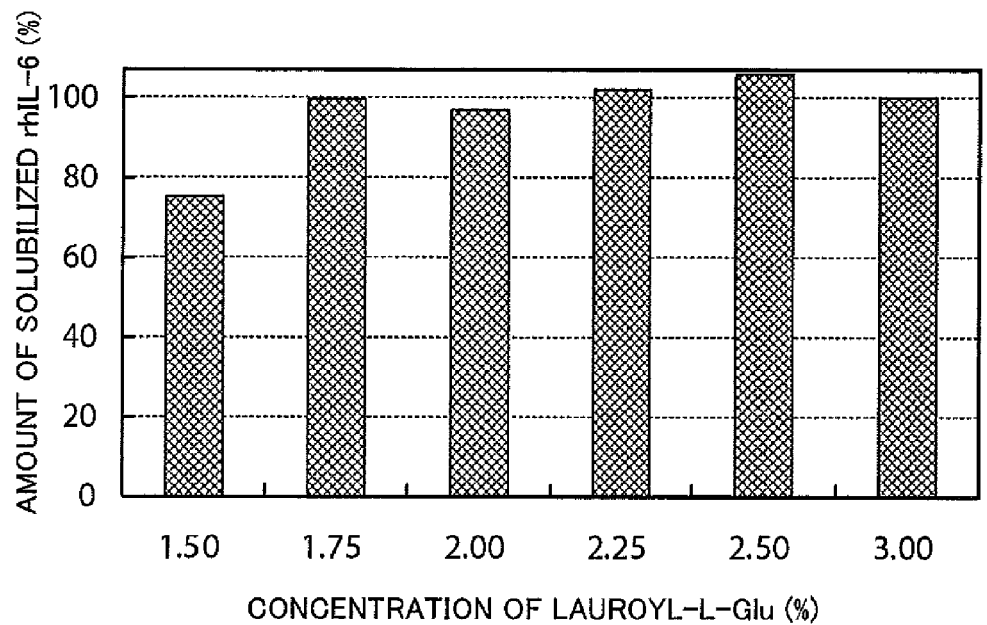
FIG. 3 shows effect of the concentration of lauroyl-L-Glu on the amount of solubilized rhIL-6 (Reference Example 3).

As clearly shown in FIG. 3, it was found that, when the concentration of lauroyl-L-Glu was 1.50%, although not as high as the amount of rhIL-6 extracted and solubilized with 3.00%, an extraction amount of a little less than 80% thereof could be obtained. When the concentration of lauroyl-L-Glu was 1.75% or higher, an extraction amount almost as high as when carrying out the extraction and solubilization with 3.00% was obtained. From these results, it was found that a protein having a level of hydrophobicity equivalent to that of rhIL-6 can be extracted with lauroyl-L-Glu at a concentration of 1.50%, and can be extracted as well with lauroyl-L-Glu at a concentration of 3.00%.

Reference Example 4

In Step (2), the optimal concentration of a surfactant during refolding by diluting a protein extracted with the surfactant was investigated. Since rhIL-6 provides a fluorescence spectrum which greatly reflects the higher-order structure, the maximum fluorescence intensity of rhIL-6 and its wavelength in various concentrations of lauroyl-L-Glu were traced to determine the concentration of lauroyl-L-Glu suitable for the refolding.

Figure 4:
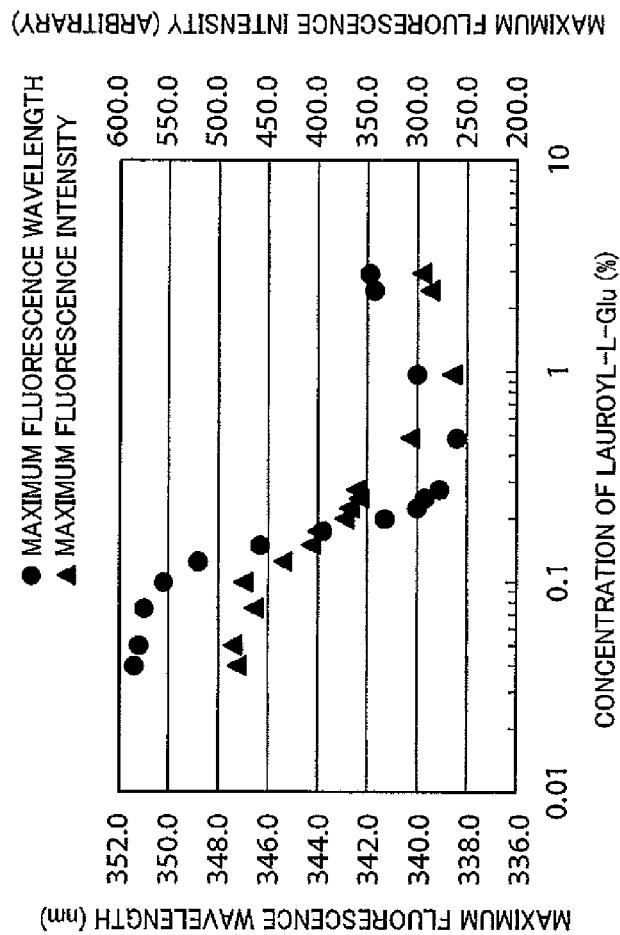
FIG. 4 shows the relationship between the concentration of lauroyl-L-Glu and the maximum fluorescence wavelength and the maximum fluorescence intensity (Reference Example 4).

A rhIL-6 preparation (Japanese Patent No. 3200850) was adjusted to 0.075 mg/ml in 10 mM sodium phosphate, pH 7.0, and the fluorescence spectrum was measured at room temperature with an excitation wavelength of 295 nm and a fluorescence wavelength of 315 nm to 420 nm (FP-6500 spectrofluorometer, available from JASCO). The results are shown in FIG. 4.

When the concentration of lauroyl-L-Glu was 0% to 0.1%, both of the maximum fluorescence wavelength and fluorescence intensity of rhIL-6 hardly changed. This suggested that, in this concentration range, bonding of lauroyl-L-Glu hardly occurred, and, even if slight bonding occurred, the structure of rhIL-6 would not be changed from the native state to a different state.

When the concentration of lauroyl-L-Glu was 0.125% to 0.275%, the maximum fluorescence wavelength shifted gradually and continuously towards the lower wavelength (ultraviolet shift). This suggested that, in this concentration range, as bound with lauroyl-L-Glu, rhIL-6 changed into a structural state having a certain maximum fluorescence intensity and its wavelength.

When the concentration of lauroyl-L-Glu exceeded 0.967%, the maximum fluorescence wavelength shifted to the higher wavelength (infrared shift). This suggested that, in this concentration range, the higher-order structure of rhIL-6 became more open, that is, the higher-order structure of rhIL-6 began to be lost.

From the results above, it was found that the higher-order structure of the protein can be guided perfectly to the native state by dilution to achieve the concentration of lauroyl-L-Glu of lower than 0.1%, and that the higher-order structure can be guided close to the native state by dilution to achieve a concentration of 0.125% to 0.275%.

Reference Example 5

It was confirmed that the relationship between the concentration of lauroyl-L-Glu and the higher-order structure of rhIL-6, which was revealed in Reference Example 4, was observed as well in the process of stepwise dilution (refolding process) from the state of rhIL-6 dissolved in a surfactant as the starting point.

A rhIL-6 preparation (Japanese Patent No. 3200850) was adjusted to 3 mg/ml in 10 mM sodium phosphate (pH 7.0 at 25° C.) containing 2% lauroyl-L-Glu. This solution was subjected to stepwise dilution with 10 mM sodium phosphate (pH 7.0 at 25°), thereby preparing a concentration gradient of 1.0%, 0.3%, 0.1%, and 0.05% of lauroyl-L-Glu. After the concentration of rhIL-6 in each of the diluted solutions was adjusted to 0.075 mg/ml, the fluorescence spectra of the respective diluted solutions were measured to trace the change in the maximum fluorescence wavelength that occurs with the change in the concentration of lauroyl-L-Glu.

Figure 5:
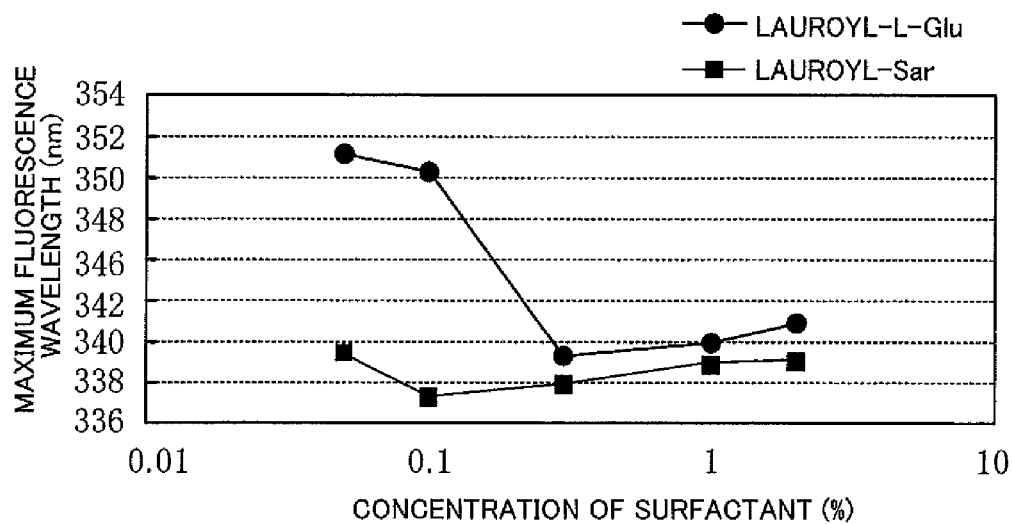
FIG. 5 shows change in the maximum florescence wavelength in accordance with the change in the concentration of lauroyl-L-Glu (Reference Example 5).

For comparison, the same operation was carried out using lauroyl-Sar instead of lauroyl-L-Glu. The results are shown in FIG. 5.

When the concentration of lauroyl-L-Glu is 2 to 0.3%, the maximum fluorescence wavelength was around 340 nm, that is, the higher-order structure of rhIL-6 was still in a state different from the native state. On the other hand, the maximum fluorescence wavelength was as high as 350 nm at 0.1% and 0.05%, and, therefore, it was found that the native higher-order structure of rhIL-6 was actually restored with lauroyl-L-Glu at these concentrations, that is, rhIL-6 was refolded. As for lauroyl-Sar used for comparison, the maximum fluorescence wavelength did not change at all within the concentration range investigated; therefore, no refolding was observed.

Example 1

Step (1): Solubilization of Denatured Protein with Surfactant

The same water-insoluble granules as used in Reference Example 1 were added to 5 ml of 2.5% lauroyl-L-Glu solution (containing 10 mM sodium phosphate, pH 7 at 25° C.), and this mixture was incubated at 37° C. for 1 hour, thereby extracting rhIL-6 from the insoluble granules and solubilizing rhIL-6. The concentration of rhIL-6 in the obtained solubilized solution was 6.5 mg/ml.

Step (B): Formation of Disulfide Bond:

Reduced glutathione and oxidized glutathione were added to the obtained solubilized solution to achieve the concentrations of 10 μM and 2 μM, respectively, and this mixture was incubated at room temperature for 18 hours to allow formation of an intramolecular disulfide bond.

Step (2): Dilution with Additive Solution

In the meantime, the additive arginine hydrochloride was added to a 10 mM sodium phosphate aqueous solution to prepare diluting solutions (pH 7.0 at 25° C.) having concentrations of arginine hydrochloride of 0.4 M, 0.8 M, and 1.2 M, respectively. As a negative control, a diluting solution prepared in the same manner except without the additive was prepared.

An aliquot of 0.1 ml of the solubilized solution incubated for 18 hours was diluted 50 times with each of these diluting solutions to adjust the concentration of lauroyl-L-Glu to 0.05%.

In the same manner as in Reference Example 1, the relationship between the additive concentration and the percentage of refolding of rhIL-6 was evaluated using ion-exchange HPLC. The results are shown in Table 1.

Comparative Examples 1 to 2

In the same manner as in Example 1 except using sucrose and glycerol instead of arginine hydrochloride as the additive, the relationship between the additive concentration and the percentage of rhIL-6 refolding was evaluated using ion-exchange HPLC. The results are shown in Table 1.

Comparative Example 3

Refolding of rhIL-6 was carried out similar to that described in Example 1 of Japanese Patent No. 3200850. Specifically, the same water-insoluble granules as used in Example 1 were added to 5 ml of 6 M guanidine chloride (pH 7 at 25° C.), and this mixture was incubated at 37° C. for 1 hour, thereby extracting rhIL-6 from the insoluble granules and solubilizing rhIL-6. The concentration of rhIL-6 in the obtained solubilized solution was 0.88 mg/ml.

Subsequently, the obtained solubilized solution was subjected to exchange of the buffer to 10 mM sodium acetate, pH 5.0 using a Sephadex G-25 column. In the same manner as in Example 1, the percentage of refolding of rhIL-6 was evaluated using ion-exchange HPLC. The results are shown in Table 1.

TABLE 1

|  | Additive | Amount of rhIL-6 (%) |
| --- | --- | --- |
| Comparative Example 3 | Example 1 of Japanese Patent No. 3200850 | 100 |
| Negative Control | Not added | 125 |
| Example 1 | 0.4M arginine hydrochloride | 166 |
|  | 0.8M arginine hydrochloride | 174 |
|  | 1.2M arginine hydrochloride | 176 |
| Comparative Example 1 | 0.4M sucrose | 113 |
|  | 0.8M sucrose | 151 |
|  | 1.2M sucrose | 136 |
| Comparative Example 2 | 0.4M glycerol | 128 |
|  | 0.8M glycerol | 135 |
|  | 1.2M glycerol | 137 |

The values in Table 1 are relative to the percentage of refolding of rhIL-6 by the previously reported technology shown in Comparative Example 3 as a standard.

In the case of the negative control, that is, using the diluting solution containing no additive, the percentage of refolding was 125% as compared to the previously reported technology; therefore, the superiority was obvious.

The percentage of refolding reached 166% when arginine hydrochloride was added at a level of 0.4 M to the diluting solution, and the percentage of refolding was dramatically increased to 174% and 176% as the concentration of arginine hydrochloride was increased to 0.8 M to 1.2 M, respectively.

Alternatively, even when either sucrose or glycerol, which are considered to facilitate protein refolding, was added, the improvement was only slight compared to arginine hydrochloride (Comparative Examples 1 to 2).

Thus, it was found that, when a protein is solubilized with lauroyl-L-Glu and the solubilized solution is diluted for refolding, the addition of arginine hydrochloride to the diluting solution increased the percentage of protein refolding.

Example 2

Step (1): Solubilization of Denatured Protein with Surfactant

In the same manner as in Example 1, except for changing the concentration of lauroyl-L-Glu in the lauroyl-L-Glu aqueous solution to 2.5% and the pH to 8.5, rhIL-6 was solubilized. The concentration of rhIL-6 in the obtained solubilized solution was 6.5 mg/ml.

Step (B): Formation of Disulfide Bond:

Subsequently, in the same manner as in Example 1, the obtained solubilized solution was incubated in the presence of reduced glutathione at a concentration of 10 μM and oxidized glutathione at a concentration of 2 μM at room temperature for 18 hours.

Step (2): Dilution with Additive Solution

Arginine hydrochloride or N-α-butyroylarginine (Nα-butyroyl-L-arginine) was added as an additive to 10 mM sodium phosphate aqueous solution to prepare a diluting solution having an additive concentration of 0.4 M or 0.8 M (pH 7.0 at 25° C.). In this case, N-butyroylarginine was prepared by the following method: after dissolving arginine in water/2-propanol, the reaction system was adjusted to pH 11 at 10 to 15° C. While maintaining the temperature and the pH with sodium hydroxide, the reaction system was reacted with butyroyl chloride, which was added in a stepwise manner. After the termination of the reaction, the solution was purified using a cation-exchange resin, and a white solid was obtained. The structure and purity thereof were confirmed using reverse-phase HPLC and $^1$H-NMR. As a negative control, a diluting solution was prepared in the same manner except for not adding an additive.

An aliquot of 0.1 ml of the solubilized solution incubated at room temperature for 18 hours was diluted 40 times with each of these diluting solutions, and thereby the concentration of lauroyl-L-Glu was adjusted to 0.05%.

In the same manner as in Example 1, the relationship between the additive concentration and the percentage of rhIL-6 refolding was evaluated using ion-exchange HPLC. The results are shown in Table 2.

TABLE 2

| | Additive | Amount of rhIL-6 (%) |
|---|---|---|
| Comparative Example 3 | Example 1 of Japanese Patent No. 3200850 | 100 |
| Negative Control | Not added | 115 |

TABLE 2-continued

| | Additive | Amount of rhIL-6 (%) |
|---|---|---|
| Example 2 | 0.4M arginine hydrochloride | 157 |
| | 0.8M arginine hydrochloride | 188 |
| | 0.4M N-butyroyl arginine | 179 |
| | 0.8M N-butyroyl arginine | 175 |

The values in Table 2 are relative to the percentage of refolding of rhIL-6 by the previously reported technology shown in Comparative Example 3 as a standard.

The percentage of refolding was 115% when no additive was added to the diluting solution, whereas the percentage of refolding was dramatically increased to 157% and 188% when arginine hydrochloride was added at concentrations of 0.4 M and 0.8 M, respectively, as an additive.

In the meantime, when the additive N-butyroylarginine was added at a concentration of 0.4 M, the percentage of refolding reached 179%; therefore, the percentage of refolding was largely improved compared to when no additive was added to the diluting solution, which resulted in 115%, and where arginine hydrochloride was added at the same concentration (0.4 M).

N-butyroylarginine is ampholytic at neutral pH and therefore loses the net charge. Accordingly, even if N-butyroyl arginine is added at a concentration of 0.4 M or higher, a diluted solution containing N-butyroylarginine does not need to be diluted, and can be directly loaded onto an ion-exchange chromatography to purify and recover a refolded protein. Therefore, it is considered that N-butyroylarginine can be used more efficiently than arginine hydrochloride.

Example 3

Step (1): Solubilization of Denatured Protein with Surfactant

Water-insoluble granules of transglutaminase (protein-glutamine, γ-glutamyltransferase, EC 2.3.2.13; U.S. Pat. No. 6,833,258) prepared in recombinant E. coli were added to 5 ml of 2.0% lauroyl-L-Glu aqueous solution (10 mM tris hydrochloride, 20 mM DTT, pH 8.5 (25° C.)), and the mixture was incubated at 37° C. for 1 hour, thereby extracting and solubilizing transglutaminase. The concentration of transglutaminase in the obtained solubilized solution was 6.98 mg/ml.

Step (A): Dilution Before Dilution with Additive Solution

An aliquot of 0.1 ml of the obtained solubilized solution was diluted 40 times with 10 mM sodium phosphate (pH 7.0 at 25° C.) to adjust the concentration of lauroyl-L-Glu to 0.05%, and then the obtained diluted solution was incubated at room temperature for 2 hours.

Step (2): Dilution with Additive Solution

Arginine hydrochloride was added as an additive to the diluted solution ("without dilution to 1%" in Table 3). As a negative control, a diluted solution containing no additive was prepared. An aliquot of 0.1 ml of the solubilized solution was diluted with 10 mM sodium phosphate (pH 7.0 at 25° C.) to adjust the concentration of lauroyl-L-Glu to 0.05%.

In the meantime, 0.1 ml of the obtained solubilized solution was diluted 2 times with 0.6 M sodium phosphate (pH 7.0 at 25° C.) to adjust the concentration of lauroyl-L-Glu to 1.0%, and this solution was incubated at room temperature for 30 minutes. Subsequently, the solution was diluted with 10 mM sodium phosphate (pH 7.0 at 25° C.) to adjust the concentration of lauroyl-L-Glu to 0.05%, and this diluted solution was incubated at room temperature for 2 hours. Arginine hydrochloride was added to the diluted solution ("with dilution to 1%" in Table 3). As a negative control, a diluted solution containing no additive was prepared. An aliquot of 0.1 ml of the obtained solubilized solution was diluted 2 times with 0.6 M sodium phosphate (pH 7.0 at 25° C.) to adjust the concentration of lauroyl-L-Glu to 1.0%, and this diluted solution was incubated at room temperature for 30 minutes. Subsequently, the solution was diluted with 10 mM sodium phosphate (pH 7.0 at 25° C.) to adjust the concentration of lauroyl-L-Glu to 0.05%, and this solution was incubated at room temperature for 2 hours (no additive added to the diluted solution).

The relationship between the concentration of arginine hydrochloride and the percentage of refolding of transglutaminase was confirmed using gel-filtration HPLC (column: Superdex 75HR 10/30, available from GE Healthcare UK Ltd.; eluent: 0.2 M sodium phosphate, pH 7.0; flow rate: 1 ml/min.). The results are shown in Table 3.

TABLE 3

| Concentration of arginine hydrochloride (M) | Concentration of transglutaminase (μg/ml) | |
|---|---|---|
| | Without dilution to 1% | With dilution to 1% |
| 0 | 43 | 46 |
| 0.4 | 100 | 96 |
| 0.8 | 120 | 143 |
| 1.2 | 127 | 151 |

When no arginine hydrochloride was added to the diluted solution, the concentration of transglutaminase confirmed in gel-filtration HPLC did not reach 50 μg/ml when diluted to 1% and then to 0.05%, and when diluting to 0.05% without dilution to 1%. Moreover, when these diluted solutions were continued to be incubated at room temperature, transglutaminase gradually disappeared. Accordingly, it was found that the native higher-order structure of transglutaminase was not restored.

In the meantime, when arginine hydrochloride was added at a concentration of 0.4, 0.8, or 1.2 M at the time of the dilution, the concentration of transglutaminase increased depending on the concentration of added arginine hydrochloride, and did not disappear even when maintained at room temperature.

Furthermore, even when adding arginine hydrochloride at the same concentration, it was shown that the concentration of transglutaminase tended to be higher when diluting the extract of 2.0% lauroyl-L-Glu 2 times to 1% and then to 0.05% than when diluting to 0.05% without the dilution to 1%. In particular, when the concentrations of transglutaminase were compared when adding arginine hydrochloride at a concentration of 1.2 M, it was found that the concentration clearly increased from 127 μg/ml to 151 μg/ml.

Thus, it was found that refolding of transglutaminase was efficiently carried out by adding arginine hydrochloride at the time of the dilution and by carrying out dilution after the solubilization at first to achieve the concentration of lauroyl-L-Glu of 1% and then carrying out further dilution.

Example 4

Step (1): Solubilization of Denatured Protein with Surfactant, Step (A): Dilution Before Dilution with Additive Solution A solubilized solution of transglutaminase (the concentration of transglutaminase of 6.67 mg/ml) obtained in the same manner as in Example 3 was diluted 2 times with 0.6 M sodium phosphate (pH 7.0 at 25° C.), and the resultant diluted solution was incubated at room temperature for 30 minutes.

Step (2): Dilution with Additive Solution

Subsequently, the resultant solution was diluted 20 times with 10 mM sodium phosphate (pH 7.0 at 25° C.) to adjust the concentration of lauroyl-L-Glu to 0.05%. In order to achieve the concentration of arginine hydrochloride of 0.8 M upon adjusting the concentration of lauroyl-L-Glu to 0.05%, arginine hydrochloride was added in advance to sodium phosphate used for the second dilution (the dilution of 20 times).

The obtained diluted solution was incubated at room temperature for 2 hours. After the incubation, the concentration of transglutaminase in the diluted solution was quantified using reverse-phase HPLC (Vydac 214-TP54 (Separations Group); eluent: A/0.1% TFA, B/0.1% TFA+80% acetonitrile; flow rate: 1 ml/min; elution conditions: linear concentration gradient from 30% B to 50% B at 1.0%/min.). With the concentration of transglutaminase in the solubilized solution as a standard, the percentage of refolding after the addition of arginine hydrochloride was 77%.

Comparative Example 4

Refolding of transglutaminase was carried out by the method described in Example 9 of U.S. Pat. No. 6,833,258. Specifically, the same water-insoluble granules of transglutaminase as that used in Example 3 were dissolved in 8M urea, and the pH of the solution was adjusted to 4.0 at 5° C. This solution was diluted 50 times to adjust the urea concentration to 0.16 M. Then, the pH was adjusted to 6.0 after 2 hours to allow formation of the structure. In the same manner as in Example 4, the concentration of transglutaminase was quantified using reverse-phase HPLC. With the concentration of transglutaminase dissolved with urea in the solution as a standard, the percentage of refolding after adjusting the pH to 6.0 was 29%.

As found to be 77% in Example 4, the percentage of refolding was dramatically increased compared to 29% in Comparative Example 4 in which the previously reported technique was employed.

The enzymatic activity of transglutaminase prepared in each of the refolding methods was evaluated by a method using a synthetic substrate. It was found that the enzymatic activity of the transglutaminase prepared in Example 4 was 37.5 U/mg, whereas the enzymatic activity of the transglutaminase prepared in Comparative Example 4 was 36.8 U/mg. Therefore, the transglutaminases in both cases had an enzymatic activity exceeding 30 U/mg, which was determined to be the same as that of native transglutaminase.

Example 5

Preparation of Protein

A production system was constructed of a single-chain fragment of variable region (HyHEL-10 scFv) using an E. coli BL21 strain (DE3) as a production host (Gene 129 (1), 129-134 (1993)). The production bacterium was cultured in LB media in a Sakaguchi flask at 28° C. for 12 hours with shaking, and thereby HyHEL-10 scFv was produced and accumulated in the bacterial cells in the form of insoluble granules. The bacterial cells were collected and broken by ultrasonic disintegration, and the obtained suspension was subjected to centrifugation at 5000 g for 20 minutes to recover HyHEL-10 scFv granules. The recovered HyHEL-10 scFv granules were washed twice with 1% Triton X-100 aqueous solution, and then washed with pure water (Milli Q water) to remove Triton X-100. Approximately 30 mg of the obtained granules were suspended in 1.5 ml of acetone, and thereby lipid components were dissolved and then removed. The granules were recovered by centrifugation at 5000 g for 20 minutes, and then dried overnight under reduced pressure using a vacuum pump, thereby obtaining a pellet of insoluble granules.

Step (1): Solubilization of Denatured Protein with Surfactant

An aliquot of 15 mg was weighed out from the pellet, and 0.5 ml of 5% lauroyl-L-Glu (containing 20 mM Na phosphate, pH 8.5) were added to the aliquot. After the mixture was stirred to homogenization, 20 mM Na phosphate, pH 8.5 was immediately added to the mixture to bring the total volume to 1.0 ml using the scale on the Eppendorf tube. Solubilization was carried out at 37° C. for 30 minutes.

In order to determine the concentration of the HyHEL-10 scFv in the obtained solubilized solution, the solubilized solution was subjected to centrifugation at 22° C. at 11000 g for 10 minutes, 2.4 µl of 100 mM DTT solution (pH 7) were added to 0.2 ml of the obtained supernatant (lauroyl-L-Glu 2.5%, pH 8.5), thereby adjusting the concentration of DTT to 1.2 mM, and then the mixture was heated at 37° C. for 60 minutes. This solution was subjected to reduced SDS-PAGE (Ready Gel J available from Bio-Rad Laboratories, Inc., 10 to 20% T, and CBB staining), and to quantification using anti-von Willebrand factor monoclonal antibody (WO96/17078) with a known protein concentration as a comparison control. Consequently, the concentration of solubilized HyHEL-10 scFv was determined to be 6 mg/ml.

Step (A): Dilution Before Dilution with Additive Solution

To 0.2 ml of the solubilized solution obtained in Step (1), 0.3 ml of 20 mM Na phosphate, pH 8.0 were added to bring the total volume to 0.5 ml (the concentration of lauroyl-L-Glu of 1.0%). After stirring, the mixture was incubated at 5° C. for 30 minutes.

Step (2): Dilution with Additive Solution, Step (B): Formation of Disulfide Bond Aside from the solution of 1.0% lauroyl-L-Glu obtained in Step (A), aliquots of 0.38 ml of solution of lauroyl-L-Glu of various concentrations containing the additive arginine hydrochloride, and redox materials oxidized and reduced glutathiones were prepared.

To each of the aliquots, 0.02 mL the 1.0% lauroyl-L-Glu solution obtained in Step (A) were added to bring the final total volume to 0.4 ml (dilution of 20 times). At the time of the dilution of 20 times, the concentration of lauroyl-L-Glu was 0.05%, 0.1%, 0.125%, 0.15%, 0.175%, 0.2%, 0.3%, 0.4%, or 0.5%, the concentration of arginine hydrochloride was 0.8 M, the concentrations of oxidized and reduced glutathiones were both 1 mM, and the concentration of scFv was 0.12 mg/ml. Thereafter, the obtained dilution mixtures were incubated at 5° C. for 17 hours, and then incubated at 23° C. for 43 hours.

Figure 6:
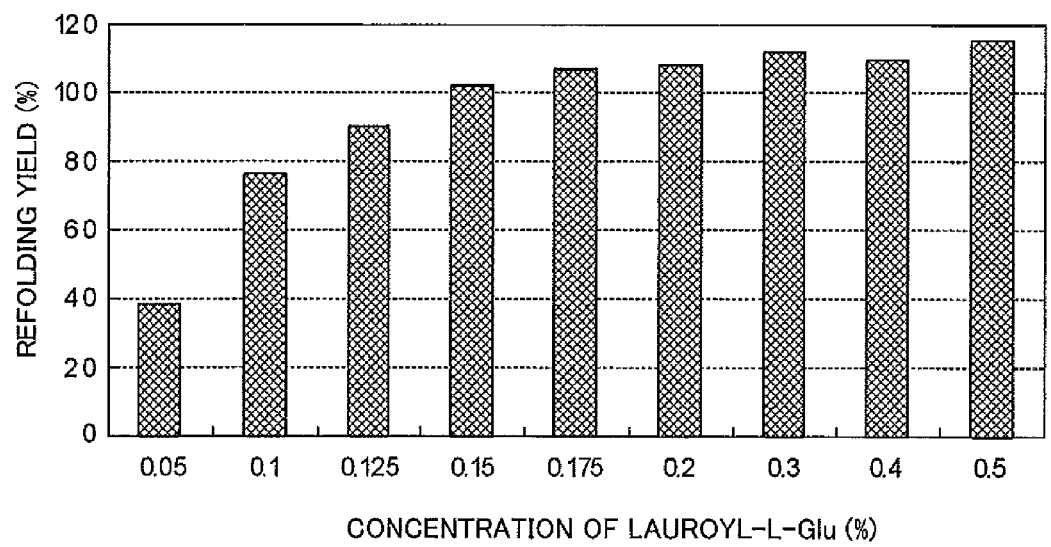
FIG. 6 shows effect of the concentration of lauroyl-L-Glu on the percentage of refolding of HyHEL-10 scFv (Example 5).

Measurement of Percentage of Refolding:

Thereafter, the percentage of refolding of HyHEL-10 scFv was calculated using gel-filtration HPLC (column: Superdex 75 GL, 10×300 mm, available from GE healthcare UK Ltd.; eluent: 0.1 M sodium phosphate, 0.2 M arginine hydrochloride, pH 6.8; flow rate: 0.8 ml/minute; extinction coefficient of scFv at 280 nm: 2.02 $cm^2$/mg). The relationship between the concentration of lauroyl-L-Glu when diluted 20 times and the percentage of the refolding is shown in FIG. 6. It was found that the percentage of the refolding was significantly dependent on the concentration of lauroyl-L-Glu, and showed an almost constant value in the range from 0.2 to 0.5%.

Figure 7:
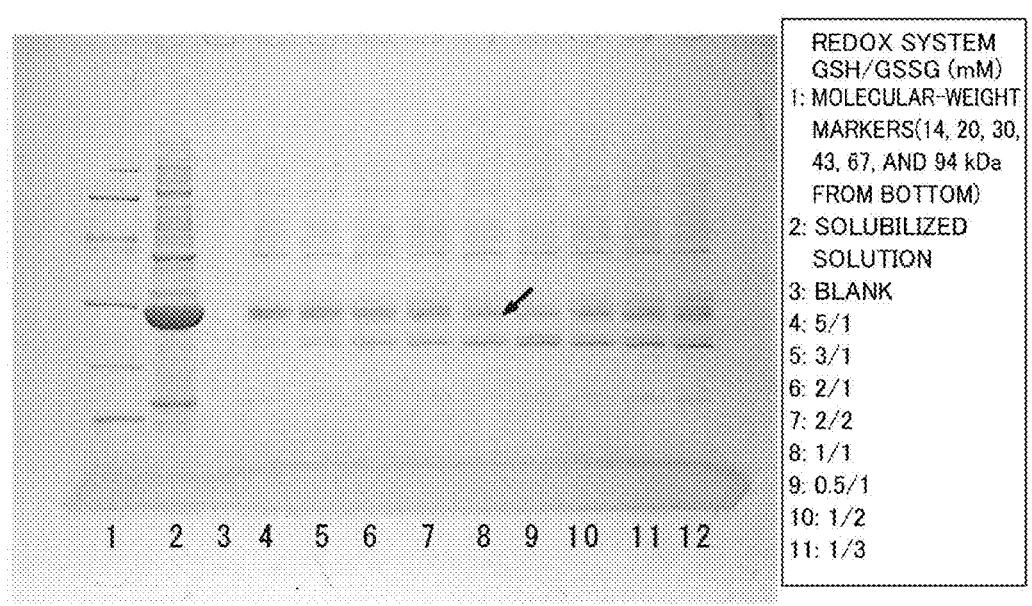
FIG. 7 shows effect of the ratio of oxidized glutathione to reduced glutathione on the percentage of refolding of HyHEL-10 scFv (Example 5).

The effect of the ratio of oxidized glutathione to reduced glutathione on the percentage of refolding was investigated using the 20-times diluted solution of lauroyl-L-Glu obtained in Step (3) (the concentration of lauroyl-L-Glu: 0.125%, the concentration of arginine hydrochloride: 0.8 M, the concentration of scFv: 0.12 mg/ml). The 20-times diluted solution was incubated at 5° C. for 17 hours, then incubated at 23° C. for 43 hours, and then subjected to non-reduced SDS-PAGE (Ready Gel J available from Bio-Rad Laboratories, 10 to 20% T, and CBB staining). The degree of progress of refolding of HyHEL-10 was investigated using the band intensity of oxidized scFv as an indicator. The result is shown in FIG. 7.

When the amount of reduced glutathione added was dominant over that of oxidized glutathione (5 mM/1 mM to 2 mM/1 mM, lane numbers 4 to 6), oxidized scFv (refolded scFv, indicated by an arrow in lane 8 in the drawing), which shows larger mobility on SDS-PAGE, a sufficiently intense band was not observed. Alternatively, when the ratio of the amount of added oxidized glutathione was increased (reduced and oxidized were 1 mM/1 mM to 1 mM/3 mM, lane numbers 8 to 11), the band of scFv showing larger mobility became more intense. However, when the amount of oxidized glutathione added was too high, the focus of the scFv band became blurred (1 mM/2 mM (lane number 10), 1 mM/3 mM (lane number 11)); therefore, it was found that some sort of mismatch occurred to the disulfide bond of scFv.

Thus, it was found that, in the case of HyHEL-10 scFv, it was appropriate to add both reduced and oxidized glutathiones at a concentration of 1 mM (lane number 8).

Example 6

Preparation of Protein

A production system was constructed of a single-chain fragment of variable region (anti-fluorescein scFv) using an *E. coli* BL21 strain (DE3) as a production host (Journal of Molecular Biology 343, 685-701 (2004)). The production bacterium was cultured in LB media in a Sakaguchi flask at 28° C. for 12 hours with shaking, and thereby anti-fluorescein scFv was produced and accumulated in the bacterial cells in the form of insoluble granules. The bacterial cells were collected and broken by ultrasonic disintegration, and the obtained suspension was subjected to centrifugation at 5000 g for 20 minutes to recover anti-fluorescein scFv granules. The recovered anti-fluorescein scFv granules were washed twice with 1% Triton X-100 aqueous solution, and then washed with pure water (Milli Q water) to remove Triton X-100. Approximately 30 mg of the obtained granules were suspended in 1.5 ml of acetone, and thereby lipid components were dissolved and then removed. The granules were recovered by centrifugation at 5000 g for 20 minutes, and then dried overnight under reduced pressure using a vacuum pump, thereby obtaining a pellet of insoluble granules.

Step (1): Solubilization of Denatured Protein with Surfactant

An aliquot of 15 mg was weighed out from the pellet, and 0.5 ml of 5% lauroyl-L-Glu (containing 20 mM Na phosphate, pH 8.5) were added to the aliquot. After the mixture was stirred to homogenization, 20 mM Na phosphate, pH 8.5 was immediately added to the mixture to bring the total volume to 1.0 ml using the scale on the Eppendorf tube. Solubilization was carried out at 37° C. for 30 minutes.

In order to determine the concentration of the anti-fluorescein scFv thus solubilized, the solubilized solution was subjected to centrifugation at 22° C. at 11000 g for 10 minutes, 1.6 µl of 100 mM DTT solution (pH 7) were added to 0.2 ml of the obtained supernatant (lauroyl-L-Glu 2.5%, pH 8.5), thereby adjusting the concentration of DTT to 0.8 mM, and then the mixture was heated at 37° C. for 60 minutes. This solution was subjected to reduced SDS-PAGE (Ready Gel J available from Bio-Rad Laboratories, Inc., 10 to 20% T, and CBB staining), and to quantification in the same manner as in Example 5. Consequently, the concentration of solubilized anti-fluorescein scFv was determined to be 8 mg/ml.

Step (A): Dilution Before Dilution with Additive

To 0.2 ml of the solubilized solution, 0.3 ml of 20 mM Na phosphate, pH 8.0 were added to bring the total volume to 0.5 ml (the concentration of lauroyl-L-Glu of 1.0%). After stirring, the mixture was incubated at 5° C. for 30 minutes.

Step (2): Dilution with Additive, Step (B): Formation of Disulfide Bond

Aside from the solution of 1.0% lauroyl-L-Glu obtained in Step (A), aliquots of 0.38 ml of solutions of lauroyl-L-Glu containing the additive arginine hydrochloride and redox materials oxidized and reduced glutathiones were prepared.

To each of the aliquots, 0.02 ml of solution of 1.0% lauroyl-L-Glu obtained in Step (A) were added to bring the final total volume to 0.4 ml (dilution of 20 times). There were a total of 9 kinds in which the concentrations of lauroyl-L-Glu were 0.05%, 0.2%, and 0.4% for each of the concentrations of arginine hydrochloride of 0, 0.4 M, and 0.8 M, at the time of 20-times dilution. The concentrations of oxidized and reduced glutathiones were both 1 mM, and the concentration of scFv was 0.16 mg/ml. Thereafter, the mixtures were incubated at 10° C. for 17 hours, and then incubated at 23° C. for 12 hours.

Measurement of Percentage of Refolding

Figure 8:
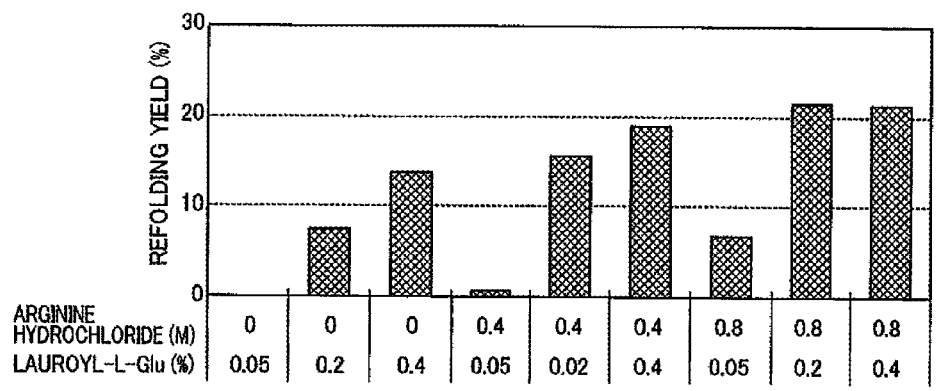
FIG. 8 shows effect of the concentration of lauroyl-L-Glu and the concentration of arginine hydrochloride on the percentage of refolding of anti-fluorescein scFv (Example 6).

Thereafter, the percentage of refolding of anti-fluorescein scFv was obtained using gel-filtration HPLC in the same manner as in Example 5 (except for using an extinction coefficient of scFv at 280 nm of 1.30 cm$^2$/mg). The relationships between the concentrations of lauroyl-L-Glu and arginine hydrochloride at the time of 20-times dilution and the percentage of the refolding are shown in FIG. 8. From FIG. 8, it was found that the percentage of refolding of anti-fluorescein scFv was significantly dependent on both arginine hydrochloride and lauroyl-L-Glu. In particular, the highest percentage of refolding was obtained when the concentration of arginine hydrochloride was set to 0.8 M, and the concentration of lauroyl-L-Glu was set to 0.2% or 0.4%.

Example 7

Step (1): Solubilization of Denatured Protein with Surfactant

A solubilized solution of insoluble granules of anti-fluorescein scFv at a concentration of 8 mg/ml (the concentration of lauroyl-L-Glu of 2.5%) was obtained in the same manner as in Example 6. To 0.08 ml of the solubilized solution, 0.64 μl of 100 mM DTT solution (pH 7) were added, thereby adjusting the concentration of DTT to 0.8 mM, and then the mixture was heated at 37° C. for 60 minutes.

Step (A): Dilution Before Dilution with Additive

To 0.08 ml of the solubilized solution, 0.12 ml of 20 mM Na phosphate, pH 8.0 were added to bring the total volume to 0.2 ml (the concentration of lauroyl-L-Glu of 1.0%). After stirring, the mixture was incubated at 5° C. for 30 minutes.

Step (2): Dilution with Additive: Step (B): Formation of Disulfide Bond

Aside from the solution of 1.0% lauroyl-L-Glu obtained in Step (A), aliquots of 0.18 ml of solutions of lauroyl-L-Glu with various concentrations containing arginine hydrochloride as an additive and oxidized and reduced glutathiones as redox reagents were prepared. The concentrations of lauroyl-L-Glu in the solutions of lauroyl-L-Glu were 0.150%, 0.225%, 0.300% and 0.375%, respectively.

To each of the aliquots, 0.02 mL of the solution of 1.0% lauroyl-L-Glu obtained in Step (A) were added to bring the final total volume to 0.4 ml (dilution of 10 times). At the time of 10-times dilution, the concentration of arginine hydrochloride was 0.8 M, the concentrations of oxidized and reduced glutathiones were 1 mM and 3 mM, respectively, and the concentration of scFv was 0.32 mg/ml. Thereafter, the mixtures were incubated at 10° C. for 17 hours.

Measurement of Percentage of Refolding

Figure 9:
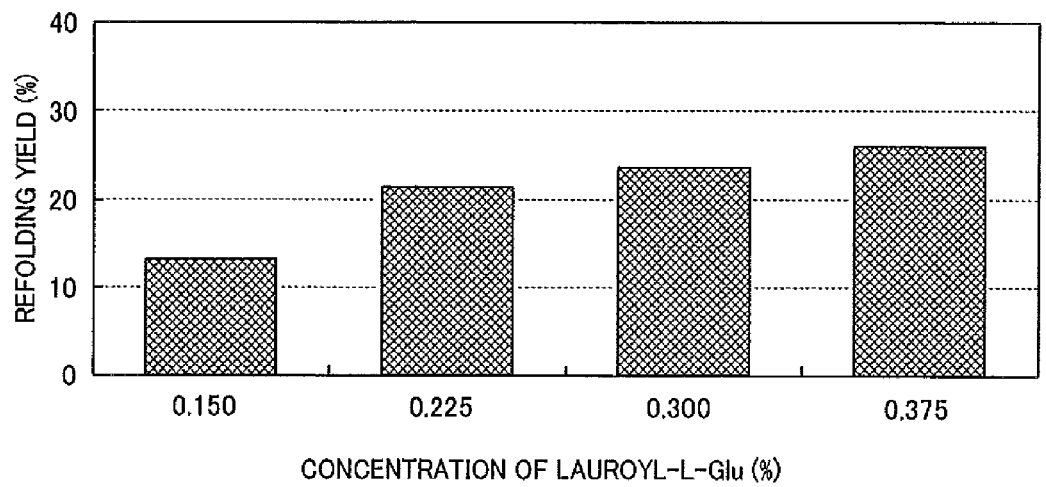
FIG. 9 shows effect of the concentration of lauroyl-L-Glu on the percentage of refolding of anti-fluorescein scFv (Example 7).

After 17 hours, the percentage of refolding of anti-fluorescein scFv was calculated using the same gel-filtration HPLC as in Example 6. The relationship between the concentration of lauroyl-L-Glu at the time of the 10-times dilution and the percentage of refolding is shown in FIG. 9.

The percentage of refolding was more improved depending on the concentration of lauroyl-L-Glu when the concentration of lauroyl-L-Glu was between 0.225 and 0.375% than that when the concentration of lauroyl-L-Glu was 0.15%. However, the improvement between 0.225 and 0.375% was not very significant. Taking into consideration the labor involved in removing lauroyl-L-Glu after the completion of refolding, it was found that adding an amount of approximately 0.3% was preferable.

Example 8

Step (1): Solubilization of Denatured Protein with Surfactant

A solubilized solution of insoluble granules of anti-fluorescein scFv at a concentration of 6 mg/ml (the concentration of lauroyl-L-Glu of 2.5%) was obtained in the same manner as in Example 6. To 0.2 ml of the solubilized solution, 1.6 μl of 100 mM DTT solution (pH 7) were added, thereby adjusting the concentration of DTT to 0.8 mM, and then the mixture was heated at 37° C. for 60 minutes.

Step (A): Dilution Before Dilution with Additive

To 0.2 ml of the solubilized solution, 0.3 ml of 20 mM Na phosphate, pH 8.0 were added to bring the total volume to 0.5 ml (the concentration of lauroyl-L-Glu of 1.0%). After stirring, the mixture was incubated at 5° C. for 30 minutes.

Step (2): Dilution with Additive, Step (B): Formation of Disulfide Bond

To 0.5 ml of the solution of 1.0% lauroyl-L-Glu obtained in Step (A), 4.5 ml of a solution of lauroyl-L-Glu containing arginine hydrochloride as an additive and oxidized and reduced glutathiones as redox materials were added (dilution of 10 times). At the time of the 10-times dilution, the concentration of lauroyl-L-Glu was 0.1%, the concentration of arginine hydrochloride was 0.8 M, the concentrations of oxidized and reduced glutathiones were both 1 mM, and the concentration of scFv was 0.24 mg/ml. Thereafter, the mixtures were incubated at 8.5° C. for 17 hours, and then heated at 45° C. for 4 hours.

Measurement of Percentage of Refolding

Figure 10:
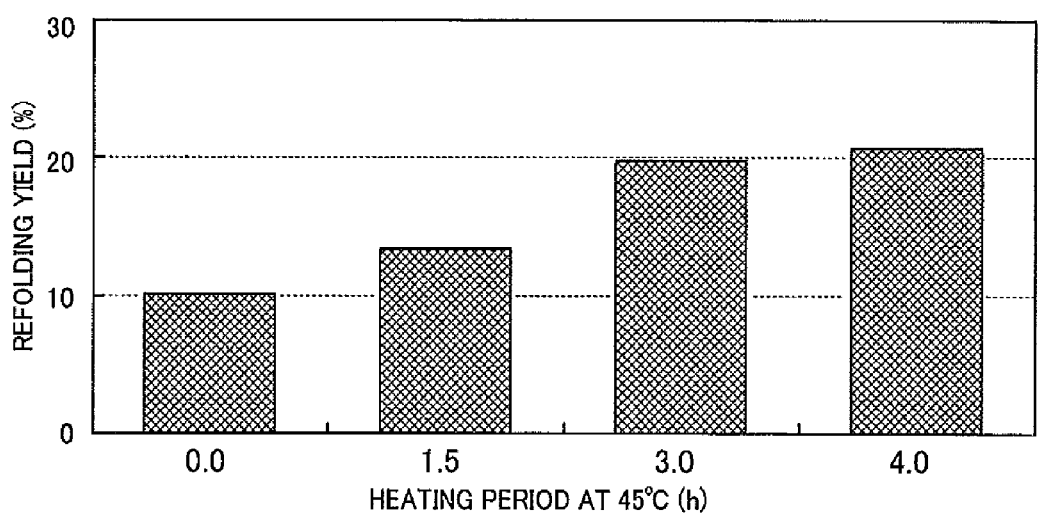
FIG. 10 shows effect of heating time on the percentage of refolding of anti-fluorescein scFv (Example 8).

Subsequently, the percentage of refolding of anti-fluorescein scFv was calculated over time using gel-filtration HPLC in the same manner as in Example 6. The result is shown in FIG. 10. The percentage of refolding reached at least 10% by the heating at 45° C., and exceeded 20% by the heating for 4 hours.

Example 9

Step (1): Solubilization of Denatured Protein with Surfactant

A solubilized solution of insoluble granules of anti-fluorescein scFv at a concentration of 6 mg/ml (the concentration of lauroyl-L-Glu of 2.5%) was obtained in the same manner as in Example 6. To 0.05 ml of the solubilized solution, 0.4 µl of 100 mM DTT solution (pH 7) were added, thereby adjusting the concentration of DTT to 0.8 mM, and then the mixture was heated at 37° C. for 60 minutes.

Step (A): Dilution Before Dilution with Additive

To 0.05 ml of the solubilized solution, 0.075 ml of 20 mM Na phosphate, pH 8.0 were added to bring the total volume to 0.125 ml (the concentration of lauroyl-L-Glu of 1.0%). After stirring, the mixture was incubated at 5° C. for 30 minutes.

Step (2): Dilution with Additive, Step (B): Formation of Disulfide Bond

Figure 11:
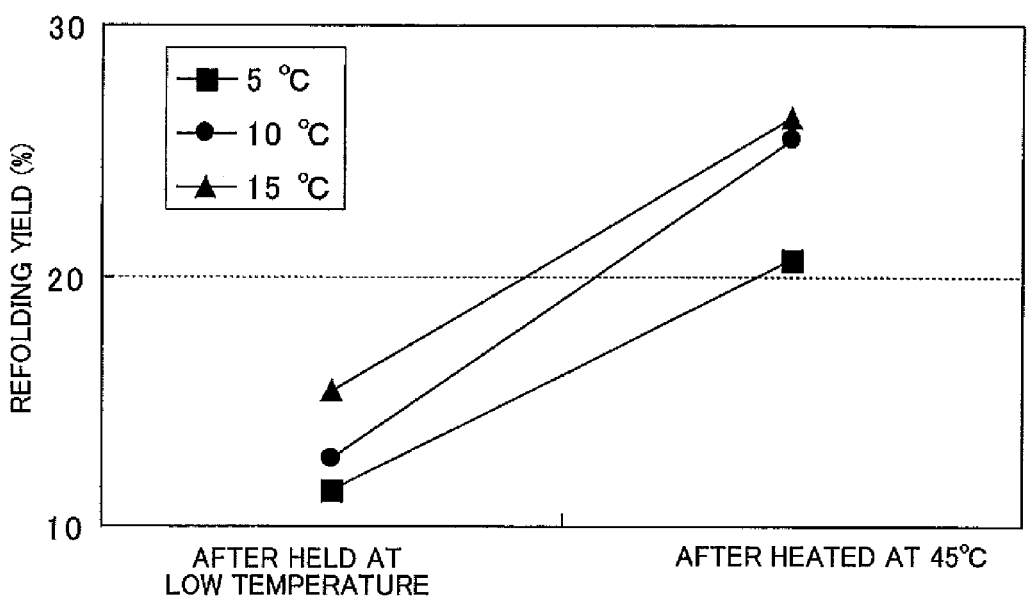
FIG. 11 shows the percentages of refolding of anti-fluorescein scFv after incubation at 5° C., 10° C., and 15° C. for 18.5 hours followed by further incubation at 45° C. for 4 hours (Example 9).

To 0.12 ml of the solution of 1.0% lauroyl-L-Glu obtained in Step (A), 1.08 ml of a solution of lauroyl-L-Glu containing arginine hydrochloride as an additive and oxidized and reduced glutathiones as redox reagents were added (dilution of 10 times) to bring the total volume to 1.2 ml. At the time of the 10-times dilution, the concentration of lauroyl-L-Glu was 0.1%, the concentration of arginine hydrochloride was 0.8 M, the concentrations of oxidized and reduced glutathiones were both 1 mM, and the concentration of scFv was 0.24 mg/ml. Three aliquots of 0.4 ml of the obtained diluted solution were incubated at 5° C., 10° C., and 15° C., respectively, for 18.5 hours. The respective percentages of refolding are shown in FIG. 11.

Figure 12:
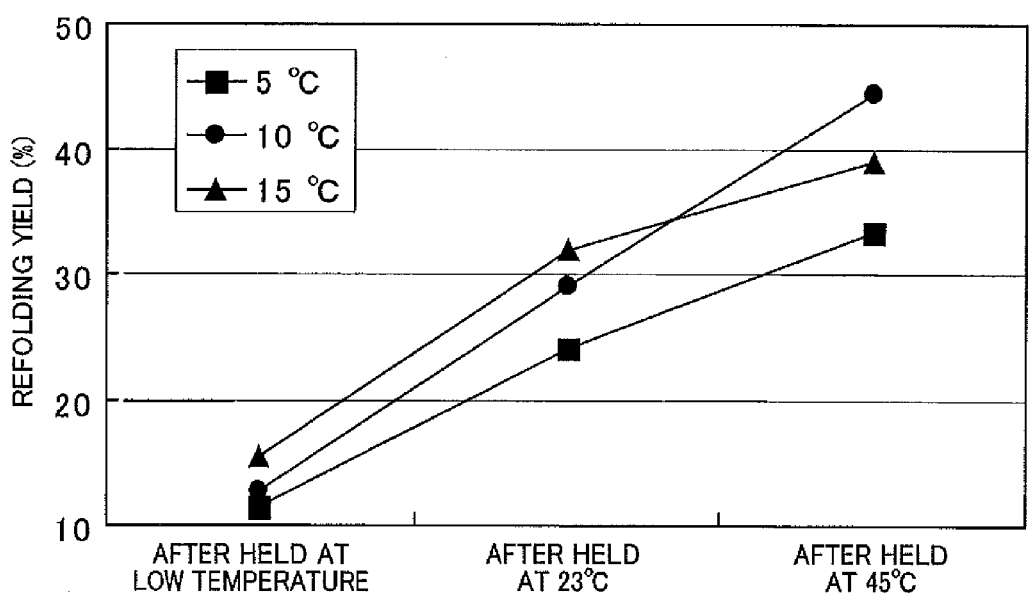
FIG. 12 shows the percentages of refolding of anti-fluorescein scFv after incubation at 5° C., 10° C., and 15° C. for 18.5 hours followed by further incubation at 23° C. for 24 hours and further subsequent incubation at 45° C. for 4 hours (Example 9).

Each of the aliquots above was further divided into two aliquots of 0.2 ml, and one was heated at 45° C. for 4 hours whereas the other one was incubated at 23° C. for 24 hours and then heated at 45° C. for 4 hours. The respective percentages of refolding are shown in FIG. 12.

It was found that, after the aliquots were incubated at 5° C., 10° C., and 15° C., respectively, for 18.5 hours, the percentages of refolding increased depending on the temperature, but only a little higher than 10%. When the aliquots were heated at 45° C. for 4 hours, the percentage of refolding increased depending on the temperature of the incubation before heating. Although the aliquot incubated at 15° C. showed the highest percentage of refolding after heating at 45° C., it was not so different from that of the aliquot incubated at 10° C. (FIG. 11).

Alternatively, when the aliquots were incubated at 5° C., 10° C., and 15° C., respectively, for 18.5 hours, then further incubated at 23° C. for 24 hours, and then heated at 45° C. for 4 hours, the percentage of refolding significantly increased compared to when the aliquot was incubated at 5° C., 10° C., and 15° C., respectively, for 18.5 hours, and then immediately heated at 45° C. It was found that, in these cases, the percentage of refolding when the first incubation was carried out at 10° C. was higher than when incubated at 15° C., and the final percentage of refolding was 45% (FIG. 12).

Thus, it was found that the highest percentage of refolding of scFv was achieved when incubation was carried out at 10° C. for 18.5 hours and then at 23° C. for 24 hours followed by heating at 45° C. for 4 hours.

Example 10

Preparation of Protein

Approximately 55 mg (18.2 mg/ml, 3 ml) of anti-von Willebrand factor monoclonal antibody (WO96/17078) dissolved in a buffer for a reaction of a digestive enzyme (papain) (20 mM sodium phosphate, 10 mM EDTA) was diluted 2 times with this buffer containing 20 mM Cys to adjust the concentration of Cys to 10 mM. To this solution, 2 ml of a suspension of an immobilized papain gel (available from Pierce Biotechnology Inc.) which had been activated in advance were added. The mixture was shaken at 37° C. for 14 hours, and subjected to centrifugation (2000 g for 5 minutes) to remove the immobilized papain gel. The solution was loaded onto HiTrap rProtein A FF (available from GE Healthcare UK Ltd.), equilibrated with PBS, and a flow-through was recovered and then concentrated using an ultrafiltration membrane (Amicon Ultra-15, molecular weight cutoff of 30 kDa, available from Millipore Corp.). Consequently, approximately 30 mg (11.5 mg/ml) of Fab (fragment of antigen binding) were added.

Step (1): Solubilization of Denatured Protein with Surfactant

To 0.5 ml of thus obtained Fab, the same volume of 5% lauroyl-L-Glu (containing 20 mM Na phosphate, pH 8.5) was added to bring the total volume to 1 ml (solution of 2.5% lauroyl-L-Glu). This solution was heated at 37° C. for 30 minutes, thereby obtaining a solubilized solution. To 0.12 ml of this solubilized solution, 1.46 µl of 100 mM DTT solution (pH 7) were added, thereby adjusting the concentration of DTT to 1.2 mM. Thereafter, the mixture was heated at 37° C. for 60 minutes (reduced modified Fab, 5.75 mg/ml).

Step (A): Dilution Before Dilution with Additive

To 0.12 ml of the thus obtained reduced modified Fab, 0.18 ml of 20 mM Na phosphate, pH 8.0 were added to bring the total volume to 0.3 ml (the concentration of lauroyl-L-Glu of 1.0%). After stirring, the mixture was incubated at 5° C. for 30 minutes.

Step (2): Dilution with Additive, Step (B): Formation of Disulfide Bond

Aside from the solution of 1.0% lauroyl-L-Glu obtained in Step (A), aliquots of 0.18 ml of solutions of lauroyl-L-Glu containing arginine hydrochloride as an additive, and oxidized and reduced glutathiones as redox materials were prepared.

To each of the aliquots, 0.02 ml of the solution of 1.0% lauroyl-L-Glu obtained in Step (A) were added to bring the final total volume to 0.2 ml (dilution of 10 times). At the time of the dilution of 10 times, there were a total of 12 kinds in which the concentrations of lauroyl-L-Glu were 0.1%, 0.2%, and 0.3% for each of the concentrations of arginine hydrochloride of 0, 0.2 M, 0.4 M, and 0.8 M. The concentrations of oxidized and reduced glutathiones were 1 mM and 5 mM, respectively, and the concentration of Fab was 0.23 mg/ml. Thereafter, thus-obtained mixtures were incubated at 10° C. for 17 hours, and then incubated at 23° C. for 24 hours.

Figure 13:
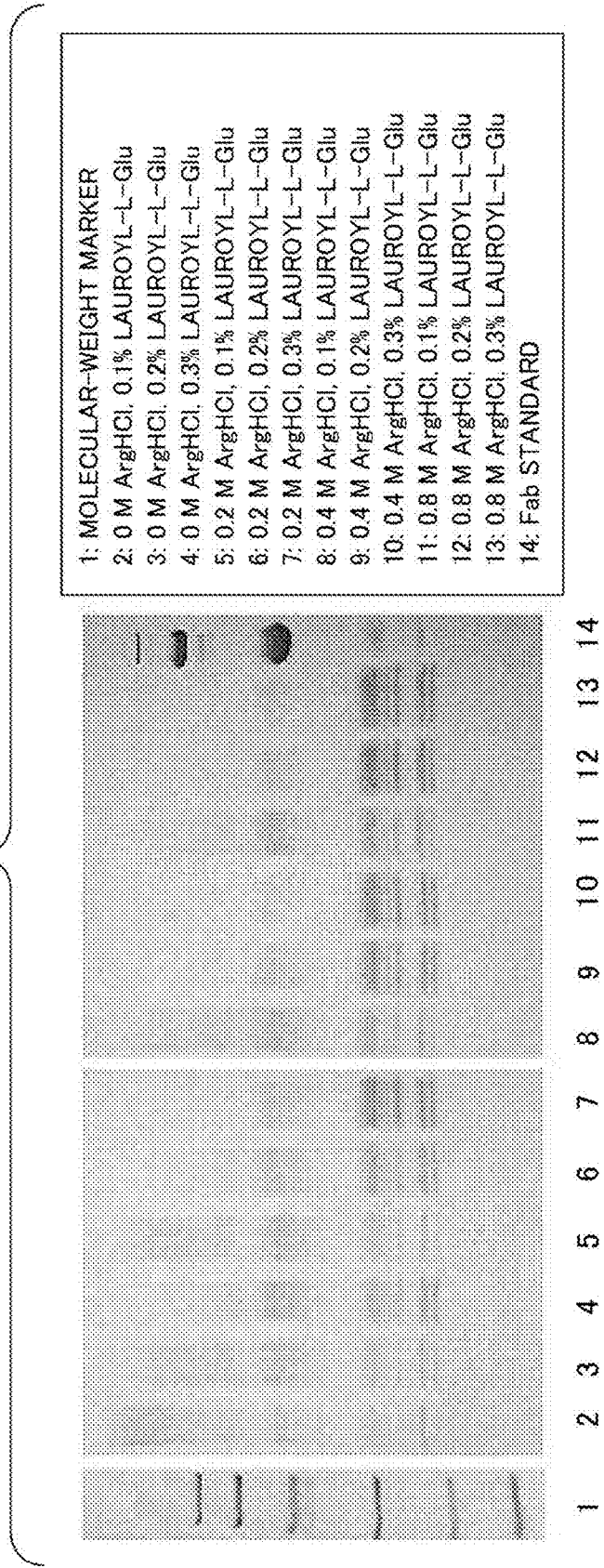
FIG. 13 shows change in the Fab band of anti-von Willebrand factor monoclonal antibody in accordance with change in the concentration of lauroyl-L-Glu and the concentration of arginine hydrochloride (Example 10).

Thereafter, a Fab band was observed in the same non-reduced SDS-PAGE as in Example 5. The result is shown in FIG. 13. When no arginine hydrochloride was added at all (lane number 2), an association/aggregation body having a high molecular weight was formed. Alternatively, when arginine hydrochloride at a concentration of at least 0.4 M or lauroyl-L-Glu at a concentration of at least 0.2% was added, formation of an association/aggregation body was significantly prevented (lane numbers 8 to 13); therefore, it was found that association/aggregation of Fab can be prevented by adding these components at appropriate concentrations. However, the target Fab band could not be observed clearly under all of these conditions.

These 12 kinds of samples were again diluted 10 times. In the solution after the dilution, the concentration of lauroyl-L-Glu was adjusted to 0.05%, the concentration of arginine hydrochloride was adjusted to 0.08 M, and the concentrations of oxidized and reduced glutathiones were adjusted to 1 mM and 5 mM, respectively. Thereafter, the solutions were incubated at 5° C. for 3 hours. Subsequently, these solutions were concentrated 10 times using ultrafiltration membrane (Amicon Ultra-15, molecular weight cutoff of 10 kDa, available from Millipore Corp.), and then incubated at 8.5° C. for 72 hours. In other words, the dilution of 10 times and the concentration of 10 times cancelled out each other, resulting in the concentration of Fab during the process being maintained at 0.23 mg/ml, which was the same as for the first dilution. A band of refolded Fab was observed in non-reduced SDS-PAGE.

Figure 14:
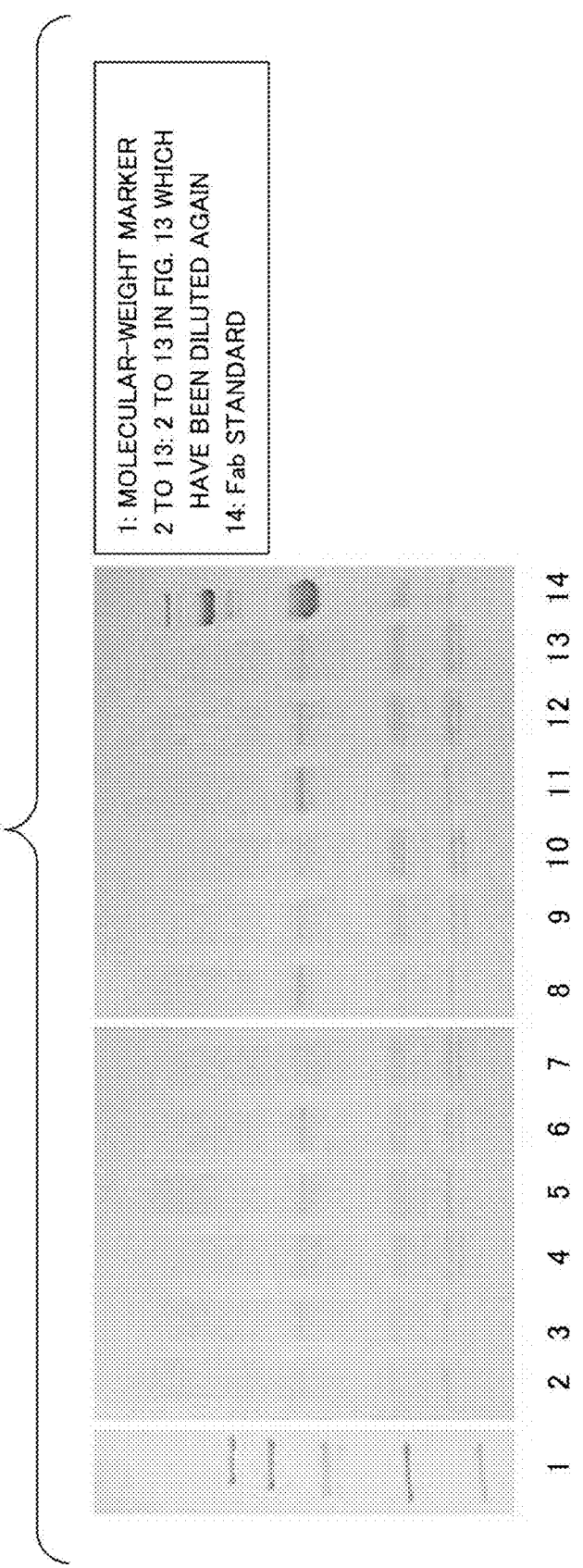
FIG. 14 shows change in the Fab band when the lane numbers 2 to 13 in FIG. 13 were diluted 10 times and then concentrated 10 times (Example 10).

As shown in FIG. 14, although the final compositions in all of the samples were the same, the clearness of the Fab band largely changed depending on the composition at the first dilution. When no arginine hydrochloride was added at the time of the first dilution, Fab was hardly refolded even after the second dilution (lane numbers 2 to 4). On the other hand, when arginine hydrochloride was added at the time of the first dilution at a concentration of 0.4 M (lane numbers 8 to 10) or 0.8 M (lane numbers 11 to 13), the strongest Fab band was observed after the second dilution; however, a suitable concentration of lauroyl-L-Glu at the time of the first dilution was 0.1% (lane numbers 8 and 11), and the Fab band became weak as the concentration was raised to 0.2% (lane numbers 9 and 12) and 0.3% (lane numbers 10 and 13).

Thus, it was found that Fab can be efficiently refolded by adjusting the concentration of arginine hydrochloride to 0.8 M and the concentration of lauroyl-L-Glu to 0.1% at the first dilution and then incubating, and then adjusting the concentration of arginine hydrochloride to 0.08 M and the concentration of lauroyl-L-Glu to 0.05% at the following dilution and incubating again.

Example 11

Step (1): Solubilization of Denatured Protein with Surfactant

In the same manner as in Example 10, 0.4 ml of a solubilized solution of Fab (a solution of 2.5% lauroyl-L-Glu) were added. To the solubilized solution, 4.85 µl of 100 mM DTT solution (pH 7) were added, thereby adjusting the concentration of DTT to 1.2 mM. The mixture was then heated at 37° C. for 60 minutes (reduced modified Fab, 5.75 mg/ml).

[Step (A): Dilution Before Dilution with Additive]

To 0.4 ml of the obtained reduced modified Fab, 0.6 ml of 20 mM Na phosphate, pH 8.0 were added to bring the total volume to 1.0 ml (the concentration of lauroyl-L-Glu of 1.0%). After stirling, the mixture was incubated at 5° C. for 30 minutes.

Step (2): Dilution with Additive Solution, Step (B): Formation of Disulfide Bond Aside from the solution of 1.0% lauroyl-L-Glu obtained in Step (A), aliquots of 0.135 ml of solutions of lauroyl-L-Glu containing arginine hydrochloride as an additive and oxidized and reduced glutathiones as redox reagents were prepared. In the solution of lauroyl-L-Glu, the concentration of lauroyl-L-Glu was 0.1%, the concentration of arginine hydrochloride was 0.8 M, and the concentration of Fab was 0.23 mg/ml, and there were a total of 6 kinds in which the concentration of reduced glutathione was 0.5 mM, 1 mM, 2 mM, or 5 mM whereas the concentration of oxidized glutathione was 1 mM, 2 mM, or 5 mM.

To each of the aliquots, 0.15 ml of the solution of 1.0% lauroyl-L-Glu obtained in Step (A) were added to bring the final total volume to 1.5 ml.

Thereafter, the diluted solutions were incubated at 10° C. for 17 hours, and then incubated at 23° C. for 6 hours. Thereafter, the solutions were diluted 10 times with buffers containing oxidized and reduced glutathiones at the same concentrations as the diluted solutions, respectively, and an appropriate amount of lauroyl-L-Glu, and a total of 6 kinds were obtained by adjusting the concentration of lauroyl-L-Glu to 0.05%, the concentration of arginine hydrochloride to 0.08 M, the concentration of oxidized glutathione to 1 mM, 2 mM, or 5 mM whereas the concentration of reduced glutathione to 0.5 mM, 1 mM, 2 mM, or 5 mM.

Thereafter, these 6 solutions were incubated at 8.5° C. for 15 hours, concentrated 10 times using an ultrafiltration membrane (Amicon Ultra-15, molecular weight cutoff of 10 kDa, available from Millipore Corp.), and incubated at 8.5° C. for 3 hours. A band of refolded Fab was observed in the same non-reduced SDS-PAGE as in Example 5.

Figure 15:
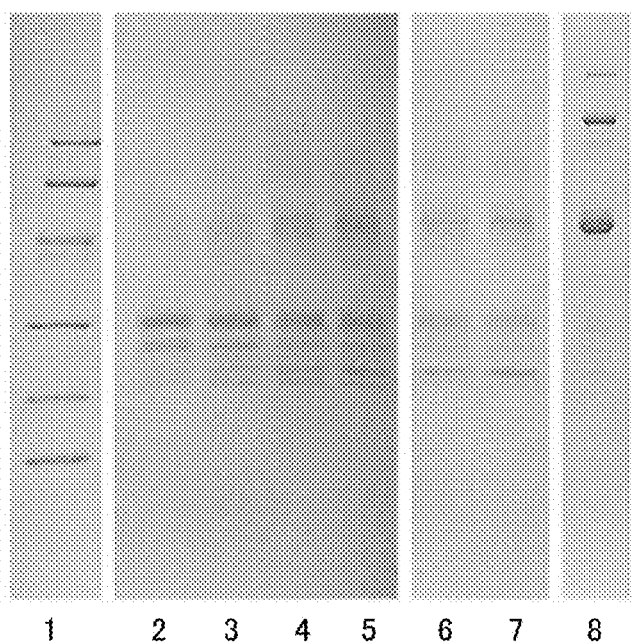
FIG. 15 shows effect of the ratio of oxidized glutathione to reduced glutathione on the Fab band of anti-von Willebrand factor monoclonal antibody (Example 11).

As shown in FIG. 15, no Fab band was formed under reducing conditions, and Fab was refolded by increasing the concentration of oxidized glutathione. Different from scFv, Fab required oxidizing conditions for its refolding. Thus, it was found that Fab can be refolded in approximately 41 hours from the first dilution when the redox conditions are appropriately adjusted.

Example 12

Preparation of Protein

A production system was constructed of an Fc-fusion protein (anti-fluorescein scFv Fc fusion) of a single-chain fragment of variable region (anti-fluorescein scFv; Journal of Molecular Biology 343, 685-701 (2004)) with an *E. coli* BL21 strain (DE3) as a production host. The production bacterium was cultured in LB media in a Sakaguchi flask at 28° C. for 12 hours with shaking, and thereby anti-fluorescein scFv Fc fusion was produced and accumulated in the bacterial cells in the form of insoluble granules. The bacterial cells were collected and broken by ultrasonic disintegration, and the obtained suspension was subjected to centrifugation at 5000 g for 20 minutes to recover insoluble granules of anti-fluorescein scFv Fc fusion. The recovered granules were washed twice with 1% Triton X-100 aqueous solution, and then washed with pure water (Milli Q water) to remove Triton X-100. Approximately 30 mg of the thus-obtained granules were suspended in 1.5 ml of acetone, and thereby lipid components were dissolved and then removed. The granules were recovered by centrifugation at 5000 g for 20 minutes, and then dried overnight under reduced pressure using a vacuum pump, thereby obtaining a pellet of insoluble granules.

Step (1): Solubilization of Denatured Protein with Surfactant

An aliquot of 15 mg was weighed out from the pellet obtained above, and 0.5 ml of 5% lauroyl-L-Glu (containing 20 mM Na phosphate, pH 8.5) were added to the aliquot. After the mixture was stirred to homogenization, 20 mM Na phosphate, pH 8.5 was immediately added to the mixture to bring the total volume to 1.0 ml using the scale on the Eppendorf tube. Solubilization was carried out at 37° C. for 30 minutes, thereby obtaining a solubilized solution.

The solubilized solution was subjected to centrifugation at 22° C. at 11000 g for 10 minutes. To 0.27 ml of the obtained supernatant, 2.7 µl of 100 mM DTT solution (pH 7) were added, thereby adjusting the concentration of DTT to 1.0 mM, and then the mixture was heated at 37° C. for 60 minutes. The obtained solution was subjected to reduced SDS-PAGE (Ready Gel J available from Bio-Rad Laboratories, 10 to 20% T, and CBB staining), and to quantification in the same manner as in Example 5. Consequently, the concentration of solubilized anti-fluorescein scFv Fc fusion was determined to be 3 mg/ml. However, in this production system, decomposition of anti-fluorescein scFv Fc fusion progressed during the culture, and the amount of anti-fluorescein scFv Fc fusion in the insoluble granules was 30% or less.

Step (A): Dilution Before Dilution with Additive

To 0.27 ml of the obtained reduced modified Fab, 0.405 ml of 20 mM Na phosphate, pH 8.0 were added to bring the total volume to 0.675 ml (the concentration of lauroyl-L-Glu of 1.0%). After stifling, the mixture was incubated at 5° C. for 30 minutes.

Step (2): Dilution with Additive, Step (B): Formation of Disulfide Bond

To 0.6 ml of the liquid obtained in Step (A), 5.4 ml of a buffer containing arginine hydrochloride as an additive and oxidized glutathione and reduced glutathione as redox materials were added to bring the total volume to 6.0 ml (dilution of 10 times). In the solution, the concentration of lauroyl-L-Glu was adjusted to 0.1%, the concentration of arginine hydrochloride was adjusted to 0.8 M, the concentrations of oxidized glutathione and reduced glutathione were adjusted to 1 mM and 5 mM, respectively, and the concentration of anti-fluorescein scFv Fc fusion was adjusted to 0.12 mg/ml.

Thereafter, the solution was incubated at 10° C. for 17 hours, and then divided into two aliquots of 0.3 ml. One was incubated at 8.5° C. for 120 hours whereas the other one was incubated at 23° C. for 120 hours.

At 48 hours and 120 hours after the incubation at each temperature was initiated, a band of refolded anti-fluorescein scFv Fc fusion was observed in non-reduced SDS-PAGE in the same manner as in Example 5.

Figure 16:
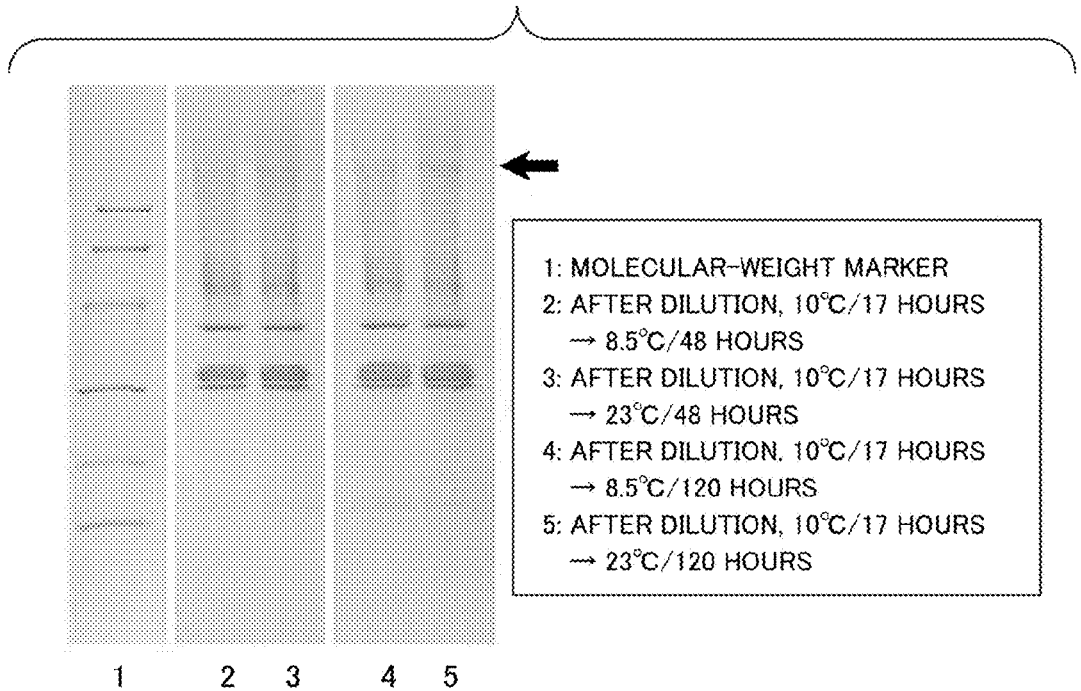
FIG. 16 shows the bands of anti-fluorescein scFv Fc fusion after incubation at 10° C. for 17 hours followed by incubation at 8.5° C. and 23° C. for 48 hours and 120 hours (Example 12).

As shown in FIG. 16, a band of anti-fluorescein scFv Fc fusion was observed after 48 hours (at the position indicated by the arrow), and the band intensity further increased after 120 hours. In both cases of incubating for 48 hours and 120 hours, after incubating at 10° C. for 17 hours, the band intensity was stronger in the case of incubating at 23° C. than when incubating at 8.5° C. It was found that the progress of refolding can be facilitated by incubating at 10° C. for 17 hours after the dilution and then raising the incubation temperature to 23° C.

Example 13

Step (1): Solubilization of Denatured Protein with Surfactant

In the same manner as in Example 5, 0.3 ml of a solubilized solution of HyHEL-10 scFv (the concentration of lauroyl-L-Glu of 2.5%, the concentration of scFv of 3.0 mg/ml) were obtained.

Step (A): Dilution Before Dilution with Additive

To the obtained solubilized solution, 0.45 ml of 20 mM sodium phosphate, pH 8.0 were added. After stirring, the mixture was incubated at 5° C. for 30 minutes (lauroyl-L-Glu of 1%).

Step (2): Dilution with Additive Solution, Step (B): Formation of Disulfide Bond To this 0.65 ml aliquot, 5.85 ml of a buffer containing each additive were added for dilution of 10 times. The concentration of lauroyl-L-Glu was adjusted to 0.3%, the concentration of arginine hydrochloride was adjusted to 0.8 M, the concentrations of oxidized glutathione and reduced glutathione were both adjusted to 1 mM, and the concentration of HyHEL-10 scFv was adjusted to 0.12 mg/ml. The mixture was incubated at 10° C. for 17 hours, and then heated at 35° C. at 2 hours.

Thereafter, the mixture was loaded onto PD-10 column (available from GE Healthcare UK Ltd.) equilibrated with 50 mM sodium phosphate, 0.2 M arginine hydrochloride, pH 8.0 to exchange the buffer, and the obtained 7.5 ml aliquot was incubated at 8.5° C. for 12 hours.

Step (C): Purification

The solution obtained as described as above was concentrated 15 times using an ultrafiltration membrane (Amicon Ultra-15, molecular weight cutoff of 10 kDa, available from Millipore Corp.), and then loaded onto Superdex 75 GL (10 mm×300 mm) equilibrated with 0.1 M sodium phosphate, 0.2 M arginine hydrochloride, pH 6.8, and thereby a purified scFv was fractionated.

Figure 17:
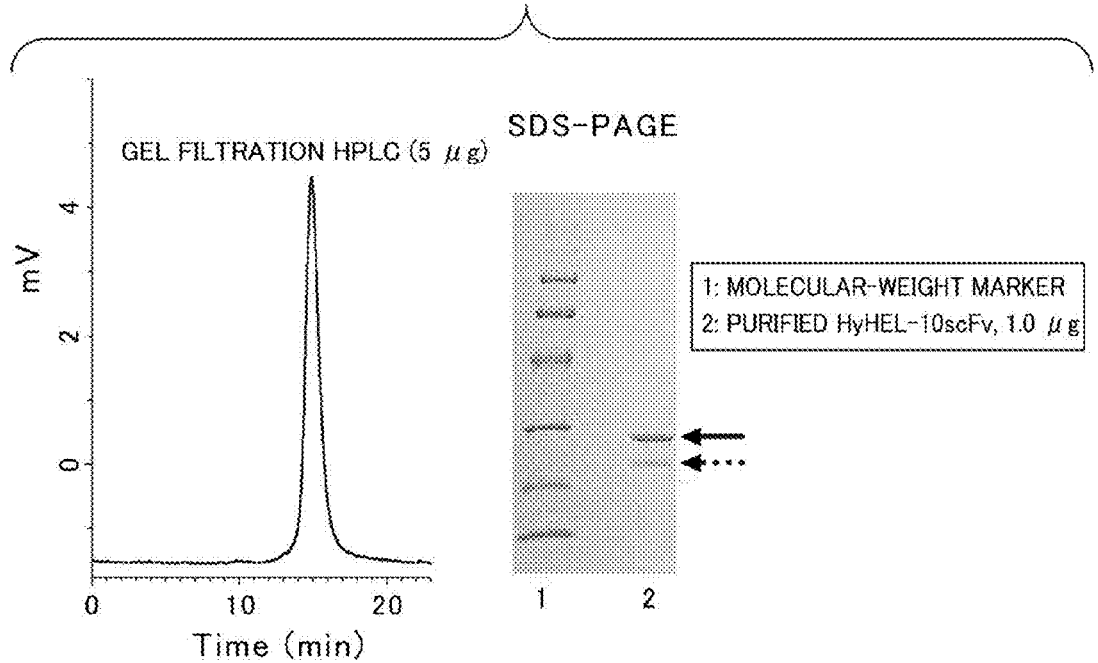
FIG. 17 shows the gel-filtration HPLC diagram and the HyHEL-10 scFv band of HyHEL-10 scFv purified with an ultrafiltration membrane (Example 13).

The obtained fraction was subjected to gel-filtration HPLC and non-reducing SDS-PAGE, which were used in Example 5, and thereby the scFv purified using the ultrafiltration membrane was confirmed to be highly pure. In the SDS-PAGE, in addition to scFv indicated by the solid line arrow, a low molecular weight component indicated by the dotted line arrow was observed. This component was a scFv fragment truncated by a residual bacterial protease derived from E. coli, and therefore not associated with the refolding in this case. The fraction obtained as described above was further subjected to field flow fractionation equipped with a multiangle light scattering detector. As a result, an observation value of the molecular weight of 33334 was obtained. This allowed confirmation that the purified scFv was forming a monomer in the aqueous solution. The result of the analysis is shown in FIG. 17.

Example 14

Step (1): Solubilization of Denatured Protein with Surfactant

In the same manner as in Example 6, 1.4 ml of a solubilized solution of anti-fluorescein scFv (the concentration of lauroyl-L-Glu of 2.5%, the concentration of scFv of 5.0 mg/ml) were obtained.

Step (A): Dilution Before Dilution with Additive

To the obtained solubilized solution, 2.1 ml of 20 mM sodium phosphate, pH 8.0 were added, and the mixture was stirred and then incubated at 5° C. for 30 minutes (lauroyl-L-Glu: 1%).

Step (2): Dilution with Additive Step (B): Formation of Disulfide Bond

To 3.45 ml of the diluted solution, 31.05 ml of a buffer containing arginine hydrochloride as an additive and oxidized glutathione and reduced glutathione as redox materials were added to bring the total volume to 34.50 ml (dilution of 10 times). In this solution, the concentration of lauroyl-L-Glu was adjusted to 0.3%, the concentration of arginine hydrochloride was adjusted to 0.8 M, the concentrations of oxidized glutathione and reduced glutathione were both adjusted to 1 mM, and the concentration of anti-fluorescein scFv was adjusted to 0.2 mg/ml.

After being incubated at 8.5° C. for 17 hours, the solution was incubated at 23° C. for 24 hours, and further heated at 45° C. for 4 hours. Thereafter, the solution was loaded onto Sephadex G25 column (5 cm×10 cm; available from GE healthcare UK Ltd.) equilibrated with PBS containing 0.2 M arginine hydrochloride to exchange buffer, and the obtained aliquot of 42 ml was incubated at 8.5° C. for 12 hours.

Step (C): Purification

An aliquot of 35 ml of the solution was concentrated 3.7 times using an ultrafiltration membrane (Amicon Ultra-15, molecular weight cutoff of 10 kDa, available from Millipore Corp.), and then the solution was loaded onto Superdex 75 pg (2.6 cm×60 cm) equilibrated with 0.1 M sodium phosphate, 0.2 M arginine hydrochloride, pH 6.8, and thereby a fraction of anti-fluorescein scFv was obtained.

Figure 18:
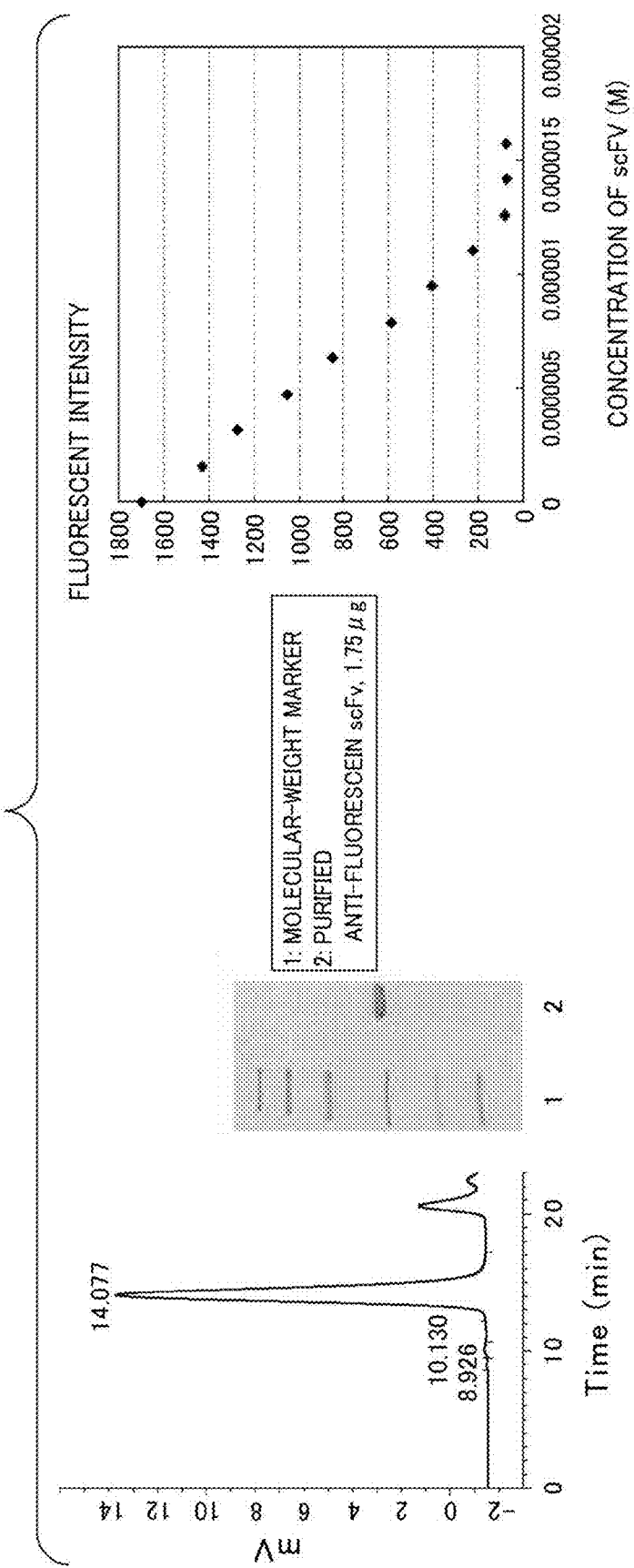
FIG. 18 shows the gel-filtration HPLC diagram and the anti-fluorescein scFv band of anti-fluorescein scFv purified with an ultrafiltration membrane (Example 14).

The obtained fraction was subjected to gel-filtration HPLC and non-reducing SDS-PAGE which were used in Example 5, and thereby the anti-fluorescein scFv was confirmed to be highly pure. The obtained fraction was further subjected to field-flow fractionation equipped with a multiangle light scattering detector. As a result, a molecular weight of 35200 was obtained. This allowed confirmation that the anti-fluorescein scFv was forming a monomer in the aqueous solution. This purified anti-fluorescein scFv (7.9 µM) was added in a stepwise manner to a solution of 0.6 µM fluorescein (available from Wako Pure Chemical Industries, Ltd.) dissolved in 100 mM tris hydrochloride, and the mixture was incubated at 23° C. for 1 hour, and then subjected to measurement of fluorescein fluorescence (excitation wavelength of 480 nm, fluorescence wavelength of 515 nm). As a result, it was found that the fluorescein fluorescence decreased in accordance with the amount of anti-fluorescein scFv added as described above. This allowed confirmation that anti-fluorescein scFv was able to re-construct the native structure. The result of the analysis is shown in FIG. 18.

Comparative Example 5

As an example of a previously reported refolding technique, HyHEL-10 and anti-fluorescein scFv were refolded using the stepwise dialysis system by Tsumoto et al. (The Journal of Biological Chemistry 278 (11), 8979-8987 (2003)).

The insoluble granules of HyHEL-10 and anti-fluorescein scFv, which were used in Example 5 and Example 9, respectively (containing 8.8 mg and 1.83 mg of scFv, respectively), were respectively suspended in 43.75 ml and 9.13 ml of 20 mM sodium phosphate (pH 8.5) containing 6M guanidine hydrochloride, and the suspensions were incubated at 37° C. for 30 minutes for solubilization of the granules.

To these, DTT was added to achieve the final concentration of 13 mM, and the mixtures were heated at 37° C. for 1 hour to reduce S—S bonds. An aliquot of 0.5 ml of each of the mixtures was subjected to sequential dialysis with 100 ml of dialysis buffer 1 to 6 at 8.5° C., and a dialyzed fraction was collected after 65 hours.

The compositions of the dialysis buffer were as follows:
1. 10 mM sodium phosphate, 6 M guanidine hydrochloride, pH 8
2. 10 mM sodium phosphate, 3 M guanidine hydrochloride, pH 8
3. 10 mM sodium phosphate, 2 M guanidine hydrochloride, pH 8
4. 20 mM sodium phosphate, 1 M guanidine hydrochloride, 0.4 M arginine hydrochloride, 1 mM oxidized glutathione, 1 mM reduced glutathione, pH 8
5. 20 mM sodium phosphate, 0.5 M guanidine hydrochloride, 0.4 M arginine hydrochloride, 1 mM oxidized glutathione, 1 mM reduced glutathione, pH 8
6. 20 mM sodium phosphate, pH 8.0.

The dialyzed fractions were subjected to centrifugation (at 12000 g for 10 minutes), and the thus obtained supernatants were loaded onto the same gel-filtration HPLC (column: Superdex 75 GL, 10×300 mm, available from GE healthcare UK Ltd.; eluent: 0.1 M sodium phosphate, 0.2 M arginine hydrochloride (pH 6.8); flow rate: 0.8 ml/min.; extinction coefficients for quantification of 2.02 $cm^2$/mg for HyHEL-10 and of 1.3 $cm^2$/mg for anti-fluorescein scFv) as in Example 5 to obtain the percentages of refolding. As a result, the percentages of refolding were found to be 9.9% for HyHEL-10 and 5.5% for anti-fluorescein scFv, largely falling below the percentages in Example 5 (the quantitative percentages of scFv recovery, FIG. 6), Example 9 (45%, FIG. 12), respectively.

The invention claimed is:

1. A method for producing a protein having a restored native higher-order structure, the method comprising:
   (1) bringing a protein which has become insoluble or lost its native higher-order structure into contact at pH 6.5 to 9.0 with a 1 to 3% aqueous solution of a surfactant selected from the group consisting of dicarboxylic acids having C8 to C16 acyl groups and salts thereof, decanoylsarcosine and salts thereof, decanoylalanine and salts thereof, decanoic acid and salts thereof, lauryltrimethylammonium chloride, and combinations thereof, to obtain a solubilized solution of the protein;
   (2) adding the solubilized solution to a buffer with pH 6.5 to 9.0 comprising an additive selected from the group consisting of arginine, an arginine derivative, and combinations thereof, wherein said additive is at a concentration of 0.05 to 1.2 M, to lower the concentration of the surfactant to 0.02 to 0.5%, to obtain a mixture; and
   (3) recovering from the mixture the protein having a restored native higher-order structure;
   wherein the dicarboxylic acids having C8 to C16 acyl groups are lauroylglutamic acid, lauroylaspartic acid, or lauroyliminodiacetic acid.

2. A method for obtaining a protein having a restored native higher-order structure , the method comprising:
   (1) bringing a protein which has become insoluble or lost its native higher-order structure into contact at pH 6.5 to 9.0 with a 1 to 3% aqueous solution of a surfactant selected from the group consisting of lauroyl glutamic acid, lauroyl aspartic acid, lauroyl iminodiacetic acid, and combinations thereof, to obtain a solubilized solution of the protein; and
   (2) adding the solubilized solution to a buffer with pH 6.5 to 9.0 comprising an additive selected from the group consisting of arginine, an arginine derivative, and combinations thereof, wherein said additive is at a concentration of 0.1 to 1.2 M, to lower the concentration of the surfactant to 0.02 to 0.275%, to obtain a mixture.

* * * * *